US007230094B2

(12) United States Patent
Chatterjee

(10) Patent No.: US 7,230,094 B2
(45) Date of Patent: Jun. 12, 2007

(54) NEUTRAL SPHINGOMYELINASE ANTISENSE RIBOZYME AND USES THEREOF

(75) Inventor: Subroto B. Chatterjee, Columbia, MD (US)

(73) Assignee: Subroto Chatterjee, Columbia, MD (US)

( * ) Notice: Subject to any disclaimer, the term of this patent is extended or adjusted under 35 U.S.C. 154(b) by 290 days.

(21) Appl. No.: 10/446,519

(22) Filed: May 27, 2003

(65) Prior Publication Data

US 2004/0006039 A1 Jan. 8, 2004

Related U.S. Application Data

(63) Continuation-in-part of application No. 10/279,215, filed on Oct. 23, 2002, now abandoned.

(60) Provisional application No. 60/342,631, filed on Oct. 23, 2001.

(51) Int. Cl.
*C07H 21/04* (2006.01)
*C12N 15/00* (2006.01)
*C12N 5/00* (2006.01)

(52) U.S. Cl. .................. 536/24.5; 435/320.1; 435/325

(58) Field of Classification Search ............... 536/23.1, 536/24.5; 514/44; 435/320.1, 325
See application file for complete search history.

(56) References Cited

U.S. PATENT DOCUMENTS 5,616,490 A * 4/1997 Sullivan et al. ............. 435/366
5,750,390 A * 5/1998 Thompson et al. ......... 435/195

OTHER PUBLICATIONS

Tonnetti et al. Journal of Experimental Medicine 1999 vol. 189, pp. 1581-1589.*
A. Alessenko, et al., "Neutral Sphingomyelinase: Localization in Rat Liver Nuclei and Involvement in Regeneration/Proliferation," Molecular and Cellular Biochemistry, vol. 143, 1995, pp. 169-174.
H. Birbes, et al., "Selective Hydrolysis of a Mitochondrial Pool of Sphingomyelin Induces Apoptosis," The FASEB Journal, vol. 14, Dec. 2001, pp. 2669-2679.
S. Chatterjee, et al., "Molecular Cloning, Characterization, and Expression of a Novel Human Neutral Sphingomyelinase," The Journal of Biological Chemistry, vol. 274, No. 52, Dec. 24, 1999, pp. 37407-37412.
S. Chatterjee, "Neutral Sphingomyelinase," Advances in Lipid Research, vol. 26, 1993, pp. 25-48.
S. Chatterjee, "Neutral Sphingomyelinase Action Stimulates Signal Transduction of Tumor Necrosis Factor-α in the Synthesis of Cholesteryl Esters in Human Fibroblasts," The Journal of Biological Chemistry, vol. 269, No. 2, Jan. 14, 1994, pp. 879-882.

S. Chatterjee, et al., "Neutral Sphingomyelinase from Human Urine: Purification and Preparation of Monospecific Antibodies," The Journal of Biological Chemistry, vol. 264, No. 21, Jul. 25, 1989, pp. 12554-12561.
S. Chatterjee, "Neutral Sphingomyelinase Increases the Building, Internalization, and Degradation of Low Density Lipoproteins and Synthesis of Cholesteryl Ester in Cultured Human Fibroblasts," The Journal of Biological Chemistry, vol. 268, No. 5, Feb. 15, 1993, pp. 3401-3406.
S. Chatterjee, "Neutral Sphingomyelinase: Past, Present and Future," Chemistry and Physics of Lipids, vol. 102, 1999, pp. 79-96.
S. Chatterjee, et al., "Oxidized Low Density Lipoprotein Stimulates Aortic Smooth Muscle Cell Proliferation," Glycobiology, vol. 6, No. 3, 1996, pp. 303-311.
S. Chatterjee, et al., "Purification of Neutral Sphingomyelinase from Human Urine," Methods in Enzymology, vol. 197, 1991, pp. 540-547.
C. Guerrier-Takada, et al., "The RNA Moiety of Ribonuclease P is the Catalytic Subunit of the Enzyme," Cell, vol. 35, Dec. 1983 (Part 2), pp. 849-857.
A. Hampel, et al., "RNA Catalytic Properties of the Minimum (−)sTRSV Sequence," Biochemistry, vol. 28, 1989, pp. 4929-4933.
A. Hampel, et al., "Hairpin' Catalytic RNA model: Evidence for Helices and Sequence Requirement for Substrate RNA," Nucleic Acids Research, vol. 18, No. 2, 1990, pp. 299-304.
Y. Hannun, "The Sphingomyelin Cycle and the Second Messenger Function of Ceramids," The Journal of Biological Chemistry, vol. 269, No. 5, Feb. 4, 1994, pp. 3125-3128.
B. Liu, et al., "Inhibition of the Neutral Magnesium-Dependent Sphingomyelinase by Glutathione," The Journal of Biological Chemistry, vol. 272, No. 26, Jun. 27, 1997, pp. 16281-16287.
S. Martin, et al., "Glycosphingolipid-Induced Cell Signaling: Apoptosis," Methods in Enzymology, vol. 363, 2003, pp. 284-299.
R. Montgomery, et al., "Inhibition of Fibrillin 1 Expression Using U1 snRNA as a Vehicle for the Presentation of Antisense Targeting Sequence," Human Molecular Genetics, vol. 6, No. 4, 1997, pp. 519-525.
F. Paris, et al., "Endothelial Apoptosis as the Primary Lesion Initiating Intestinal Radiation Damage in Mice," Science Magazine, vol. 293, Jul. 13, 2001, pp. 293-297.
L. Peña, et al., "Stress-Induced Apoptosis and the Sphingomyelin Pathway," Biochemical Pharmacology, vol. 53, 1997, pp. 615-621.
P. Peraldi, et al., "Tumor Necrosis Factor (TNF)-α Inhibits Insulin Signaling through Stimulation of the p55 TNF Receptor and Activation of Sphingomyelinase," The Journal of Biological Chemistry, vol. 271, No. 22, May 31, 1996, pp. 13081-13022.
A. Perrotta, et al., "Cleavage of Ogligoribonucleotides by a Ribozyme Derived from the Hepatitis δ Virus RNA Sequence," Biochemistry, vol. 31, No. 1, 1992, pp. 16-21.

(Continued)

*Primary Examiner*—Richard Schnizer
*Assistant Examiner*—Tracy Vivlemore
(74) *Attorney, Agent, or Firm*—Edwards Angell Palmer & Dodge, LLP; Peter F. Corless; Jonathan M. Sparks

(57) ABSTRACT

The present invention provides novel antisense ribozymes useful for inhibiting the activity of neutral sphingomyelinase. Also provided are methods for reducing the activity of neutral sphingomyelinase, as well as methods for reducing apoptosis and atherosclerosis using the ribozymes of the invention.

7 Claims, 13 Drawing Sheets

OTHER PUBLICATIONS

J. Rossi, et al., "Ribozymes as Anti-HIV-1 Therapeutic Agents: Principles, Applications, and Problems," Aids Research and Human retroviruses, vol. 8, No. 2, 1992, pp. 183-189.

P. Signorelli, et al., "Analysis and Quantitation of Ceramide," Methods in Enzymology, vol. 345, 2002, pp. 275-294.

D. Sillence, "Apoptosis and Signalling I Acid Sphingomyelinase Deficient Cells," BMC Cell Biology, vol. 2, No. 24, Nov. 12, 2001.

W. Stoffel, "Functional Analysis of Acid and Neutral Sphingomyelinases In Vitro and In Vivo, Chemistry and Physics of Lipids," vol. 102, 1999, pp. 107-121.

S. Tomiuk, et al., "Cloned Mammalian Neutral Sphingomyelinase: Functions in Sphingolipid Signaling?," Proceedings of the National Academy of Sciences of the USA, vol. 95, No. 7, Mar. 1998, pp. 3638-3643.

* cited by examiner

SEQUENCE LISTING

<160> NUMBER OF SEQ ID NOS: 3

<210> SEQ ID NO 1
<211> LENGTH: 207
<212> TYPE: RNA
<213> ORGANISM: Homo sapiens

<400> SEQUENCE: 1

| auacuuaccu | ggcaggggag | auaccaugau | cacgaaggug | guuuucccag | ggcgaggcuu | 60 |
| auccauuggc | cuccggaugu | gcugacccu  | gcgauuccc  | caaauguggg | aaacucgacu | 120 |
| gcagaauaug | ucaucauauu | gccugaugag | uccgugagga | cgaaaccucu | ucacaugaaa | 180 |
| aaguggggcu | gcguucgcgc | uuccccg    |            |            |            | 207 |

<210> SEQ ID NO 2
<211> LENGTH: 207
<212> TYPE: DNA
<213> ORGANISM: Homo sapiens

<400> SEQUENCE: 2

| cggggaagcg | cgaacgcagc | cccacttttt | catgtgaaga | ggtttcgtcc | tcacggactc | 60 |
| atcaggcaat | atgatgacat | attctgcagt | cgagtttccc | acatttgggg | aaatcgcagg | 120 |
| ggtcagcaca | tccggaggcc | aatggataag | cctcgccctg | ggaaaaccac | cttcgtgatc | 180 |
| atggtatctc | ccctgccagg | taagtat    |            |            |            | 207 |

<210> SEQ ID NO 3
<211> LENGTH: 33
<212> TYPE: RNA
<213> ORGANISM: Homo sapiens

<400> SEQUENCE: 3

| uuuucaugug | aagagguagc | aauaugauga | cau | 33 |

NEUTRAL SPHINGOMYELINASE ANTISENSE RIBOZYME AND USES THEREOF

RELATED APPLICATIONS

This application is a continuation-in-part of U.S. patent application Ser. No. 10/279,215, filed Oct. 23, 2002, now abandoned, which claims the benefit of U.S. Provisional Application Ser. No. 60/342,631, filed Oct. 23, 2001. The entire contents of each of the above-identified applications are hereby incorporated by this reference.

GOVERNMENT SUPPORT

Funding for the present invention was provided in part by the Government of the United States by virtue of grants RO-1DK 31722 by the National Institutes of Health. Accordingly, the Government of the United States has certain rights in and to the invention claimed herein.

BACKGROUND OF THE INVENTION

Sphingomyelinases type-C (E.C. 3.1.4.12) are a group of phospholipases that catalyze the hydrolytic cleavage of sphingomyelin to ceramide and phosphocholine (Chatterjee, S. (1993) *Adv. Lipid Res.* 26:25–48). Native neutral sphingomyelinase (N-SMase) purified from human urine and cultured human kidney proximal tubular cell membranes has an apparent molecular weight of 92 kDa, neutral pH optima, is heat unstable, and is localized on the surface of various cells (Chatterjee, S. (1993) supra; Chatterjee, S. et al. (1989) *J. Biol. Chem.* 264:12,534–12,561; and Chatterjee, S. et al. (1991) *Methods Enzymol., Phospholipase* 197:540–547).

Cleavage of sphingomyelin and the products of this reaction have been implicated in multiple pathways, including apoptosis, cellular growth, differentiation, and inflammatory responsiveness. Multiple forms of SMases have been described on the basis of their optimal pH and intracellular localization, including lysosomal acidic SMase (A-SMase), cytosolic $Zn^{2+}$-dependent acidic SMase, membrane-bound, magenesium-dependent neutral SMase (N-SMase), cytosolic magnesium-independent N-SMase, and alkaline SMase (Chatterjee, S. (1999) *Chem Phy. Lipids* 102, 79–9; Liu, B. and Hannun, Y. (1997) *J. Biol. Chem.* 272: 16281–16287; Martin, S. F. and Chatterjee, S. (2003) *Methods Enzymol.* (in press); Cordon-Cardo, C. and Kolesnick, R., (2001) *Science* 293–297).

N-SMase action has been shown to mediate signal transduction of vitamin $D_3$, tumor necrosis factor-α (TNF-α), interferon-gamma, and nerve growth factor (Y. Hannun, J. Biol. Chem., 269:3,125–3,128 (1994); S. Chatterjee, J. Biol. Chem., 268:3,401–3,406 (1993); and S. Chatterjee, J. Biol. Chem., 269:879–882 (1994)) leading to cell differentiation in human leukemic (HL-60) cells and insulin signaling (P. Peraldi et al., J. Biol. Chem., 271:13018–13022 (1996)). Several investigators have identified apoptosis of smooth muscle cells (SMC) in atherosclerotic plaques. Even in early stages of atherosclerosis, apoptosis of SMC occurs (Hannun, 2002. FASEB J.). The loss of these cells due to apoptosis can be detrimental for plaque stability since most of the interstitial collagen fibers, which are important for the tensile strength of the fibrous cap, are produced by SMC. It can be concluded that apoptosis in atherosclerosis is detrimental since it could lead to plaque rupture and thrombosis (Hannun, 2002. FASEB J.).

In addition to the biological roles of sphingomyelin and ceramide in signal transduction pathways involving cell regulation, recent evidence suggests that sphingomyelinases may be involved in the mobilization of cell surface cholesterol, in cholesterol ester synthesis, and in induction of low density lipoprotein (LDL) receptor activity. See S. Chatterjee, Advances in Lipid Research, 26:25–48 (1993). Recent evidence also supports a possible role of ceramide (a product of N-SMase activity) in programmed cell death and/or "apoptosis" and activation of the gene for nuclear factor (NF)-κB. See A. Alessenko and S. Chatterjee, Mol. Cell. Biochem., 143:169–174 (1995). Sphingomyelinases are also believed to serve as a signal for various exogenous effectors such as antibiotics, drugs, and growth factors, which influence the normal physiology of cells.

It has been shown previously that high concentrations of Ox-LDL (100 μg/ml) can induce the death of aortic smooth muscle cells (ASMCs). A novel aspect of Ox-LDL mediated signal transduction to explain the phenomenon above was subsequently uncovered. In ASMCs, Ox-LDL stimulates the activity of N-SMase, an enzyme that cleaves sphingomyelin to ceramide and phosphocholine. The activity of N-SMase increased 5-fold within 5 minutes of incubation of cells with Ox-LDL, but not LDL, and then returned to baseline values after 30 minutes (Chatterjee, S. et al. (1999) J. Biol. Chem. 274:37407–37412). This was accompanied by marked apoptosis in cells incubated with Ox-LDL, as evidenced by (i) a DNA laddering, (ii) [$^3$H]thymidine release, and (iii) fluorescence-assisted cell sorting analysis.

A number of specific disorders have been associated with N-SMase. For example, N-SMase has been reported to be associated with insulin resistant diabetes and obesity. See Speigel et al., J. Biol. Chem., 1996. N-SMase is also associated with malaria. The development of the malaria parasite plasmodium requires N-SMase. See Lauer et al., Proc. Nat. Acad. Sci. (USA), 1995. N-SMase also is involved in liver cell proliferation. See Alessenko, Chatterjee, Mol. Cell Biochem., 143:169–174 (1995).

Because of the involvement of N-SMase in a number of disorders, it would be desirable to have agents that are capable of downregulating N-SMase activity. However, such agents are currently not available.

SUMMARY OF THE INVENTION

The present invention, is based, at least in part, on the discovery of antisense ribozyme constructs, referred to alternately herein as "antisense ribozymes," "N-SMase ribozymes," or simply "ribozymes," which, when expressed in cells, can downregulate the activity of neutral sphingomyelinase (N-SMase). The present invention is further based, at least in part, on the discovery that the ribozymes can downregulate apoptosis mediated by proinflammatory cytokines. Accordingly, the present invention provides ribozyme molecules, as well as methods for the downregulation of N-SMase activity and apoptosis.

In one embodiment, the invention provides a nucleic acid molecule which specifically hybridizes to the mRNA encoding N-SMase, wherein the nucleic acid molecule comprises a ribozyme which is capable of cleaving the N-SMase mRNA. In a preferred embodiment, the nucleic acid molecule comprises a ribonucleotide sequence that is complementary to SEQ ID NO:3, and more preferably comprises the nucleic acid sequence of SEQ ID NO:1. In another embodiment, the invention provides a nucleic acid molecule comprising the ribozyme cDNA sequence of SEQ ID NO:2 or a complement thereof (e.g., a perfect complement), wherein SEQ ID NO:2 comprises the cDNA complement of SEQ ID NO:1. In other embodiments, the invention provides vectors and host cells (e.g., CC and C-B cells) comprising the nucleic acid molecules of the invention. In a preferred embodiment, the activity of N-SMase is downregulated in a host cell comprising the nucleic acid molecules of the invention.

In another embodiment, the invention provides methods for downregulating N-SMase activity and/or apoptosis in a cell (e.g., a smooth muscle cell) comprising introducing the ribozymes of the invention into the cells of a subject.

In another embodiment, the invention provides methods for downregulating N-SMase activity and/or apoptosis in the cells (e.g., smooth muscle cells) of a subject comprising contacting the cells of the subject with the ribozymes of the invention. In a preferred embodiment, the subject has or is at risk for atherosclerosis.

Other features and advantages of the invention will be apparent from the following detailed description and claims.

BRIEF DESCRIPTION OF THE DRAWINGS

FIG. 6 depicts a quantitative analysis of the effects of TNF-α, C$_2$-Ceramide and Fas-ligand on apoptosis in mutant (CC) and WT (MG-63) cells, as well as wild type/mock transfected cells. Cells were grown on glass cover slips and incubated for 24 hours with TNF-α (20 ng/ml), cell-permeable ceramide (C2-Ceramide) (10 ng/ml) or Fas-L (1 ng/ml). Cells were fixed and stained with DAPI and photographed at 50× magnification. Apoptotic cells were counted using a hemocytometer. The basal levels of apoptotic cells were: MG-63 (3%); L-3 (3%); and CC (2.8%). Errors bars indicate ±S.D. (N=2).

DETAILED DESCRIPTION OF THE INVENTION

Figure 1:
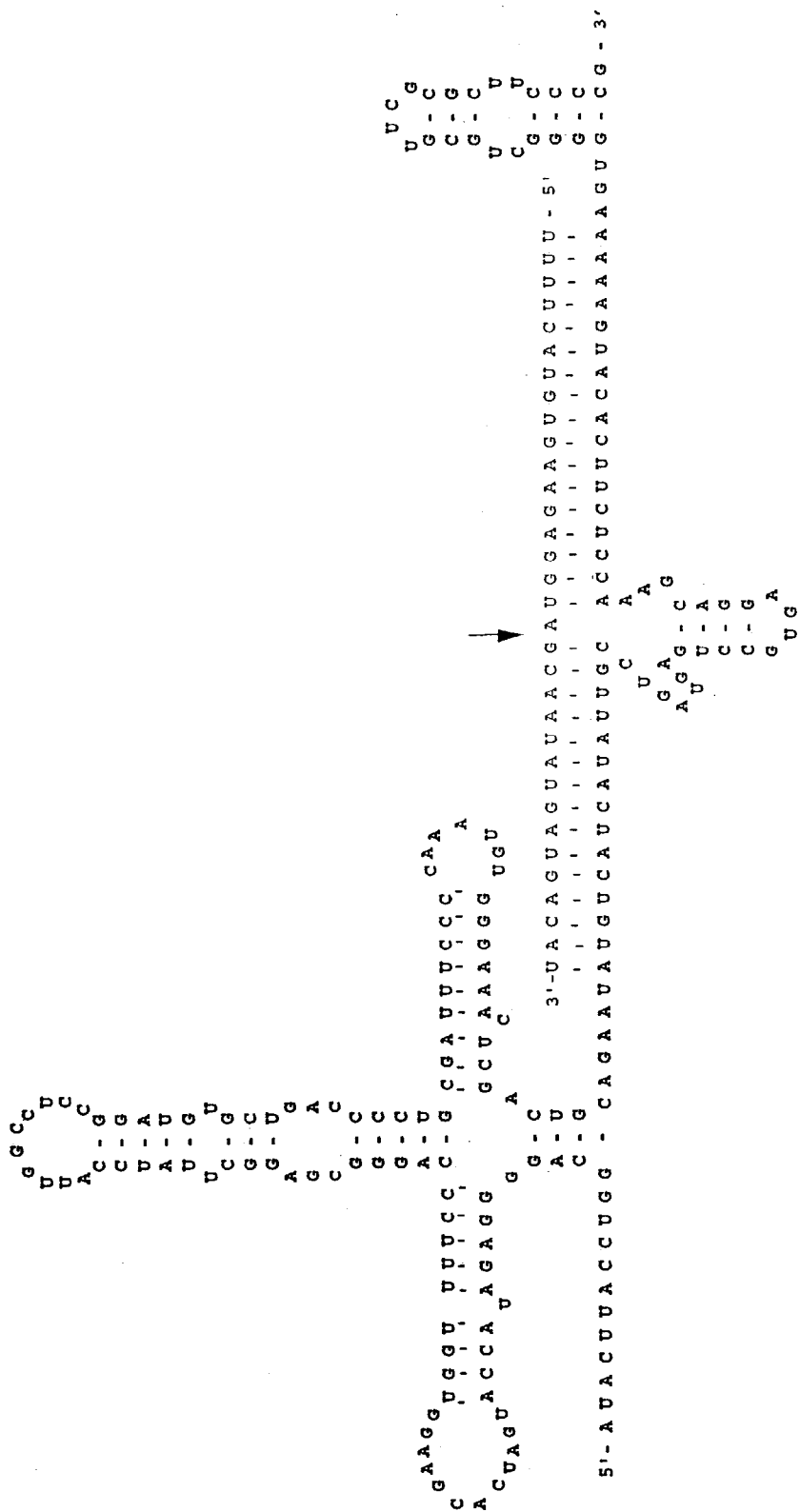
FIG. 1 depicts the nucleotide sequence (SEQ ID NO:1) and predicted secondary structure of the N-SMase hammerhead ribozyme of the invention, derived from a U1 snRNA expression cassette. The ribozyme cDNA sequence is set forth as SEQ ID NO:2. Base-pairs are indicated by dashes. The reported mRNA sequence for N-SMase (SEQ ID NO:3) is shown across from its complementary sequence in the construct. The arrow indicates the predicted site of cleavage by the hammerhead ribozyme below.

The present invention, is based, at least in part, on the discovery of antisense ribozyme constructs, referred to alternately herein as "antisense ribozymes," "N-SMase ribozymes," or simply "ribozymes," which, when expressed in cells, can downregulate the activity of neutral sphingomyelinase (N-SMase). The present invention is further based, at least in part, on the discovery that the ribozymes can downregulate apoptosis mediated by proinflammatory cytokines. Accordingly, the present invention provides ribozyme molecules, as well as methods for the downregulation of N-SMase activity and apoptosis.

Neutral sphingomyelinase (N-SMase) is a cell membrane-associated $Mg^{2+}$-dependent phospholipase that catalyzes the cleavage of sphingomyelin to form ceramide and phosphocholine. TNF-α rapidly activates N-SMase, which then acts to facilitate apoptosis in aortic smooth muscle cells (ASMCs) through the generation of ceramide and/or ceramide derivatives. In addition, transient transfection of ASMCs with an N-SMase expression vector results in enhanced sensitivity to pro-inflammatory cytokines, resulting in increased apoptosis. However, the relative importance of N-SMase in this process has not been previously fully understood. Although N-SMase has been implicated in apoptosis, agents capable of decreasing N-SMase activity have not been available. The N-SMase antisense ribozyme constructs reported here, when transfected into cultured human osteosarcoma cells, can markedly render these cells N-SMase-deficient. Furthermore, such cells become resistant to apoptosis. Thus, these studies for the first time provide "the proof of principle" that N-SMase plays a critical role in apoptosis.

Using an antisense ribozyme targeting N-SMase in an osteosarcoma cell line (MGS3), the present invention has achieved marked reduction of N-SMase activity as compared to sham-transfected cells (0.67 nmol/mg protein/hr vs. 2.7 nmol/mg protein/hr). Immunohistochemical analysis with an antibody to N-SMase and other proteins attests to the specificity of targeting. These cells remain deficient in N-SMase despite stimulation with both TNF-α and Fas ligand (Fas-L), as compared to sham-transfected cells (0.75 nmol/mg protein/hr vs. 4.0 nmol/mg protein/hr, respectively). Ceramide production was increased about 2-fold in the sham-transfected cells with this stimulation, as compared to substantially no change in the cells deficient in N-SMase. Furthermore, the sham-transfected cells developed an about 4-fold increase in apoptosis in response to either TNF-α or FAS-L stimulation, as assessed by DAPI staining. Apoptosis in response to these factors was not altered in cells deficient in N-SMase. Administration of $C_2$ ceramide (10 μm) to N-SMase-deficient cells induced an about 2.5-fold increase in apoptosis as compared to untreated cells, confirming that downstream effectors of ceramide-induced apoptosis are not disrupted in these cells. Based on these results, the antisense ribozyme directed against N-SMase can be used to abrogate the apoptosis induced by pro-inflammatory cytokines. Because smooth muscle-cells of atheromas undergo apoptosis in response to inflammation, contributing to plaque instability and predisposing plaques to rupture, the N-SMase ribozymes of the invention may provide useful agents in monitoring the pathogenesis of atherosclerosis and treating the same.

A ribozyme of the invention targets the N-SMase mRNA. Each ribozyme molecule contains a catalytically active segment capable of cleaving the N-SMase mRNA, and further comprises flanking sequences having a nucleotide sequence complementary to portions of the N-SMase mRNA. The flanking sequences serve to anneal the ribozyme to the N-SMase mRNA in a site-specific manner. Absolute complementarity of the flanking sequences to the target N-SMase mRNA sequence is not necessary, however, as only an amount of complementarity sufficient to form a duplex with the target RNA and to allow the catalytically active segment of the ribozyme to cleave at the target sites is necessary. Thus, only sufficient complementarity to permit the ribozyme to be hybridizable with the target RNA is required. Accordingly, the term "specific for the N-SMase mRNA" refers to a ribozyme containing sufficient complementarity such that the ribozyme is capable of forming a duplex with the N-SMase mRNA and allowing the catalytically active segment of the ribozyme to cleave the mRNA. Preferably, a ribozyme specific for N-SMase mRNA is capable of forming a duplex with the N-SMase mRNA and allowing the catalytically active segment of the ribozyme to cleave the mRNA under conditions such as those described in Examples 2–8, e.g., inside a cell, such that the expression and/or activity of N-SMase is downregulated.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to N-SMase mRNA, and also has enzymatic activity that is active to cleave and/or splice that mRNA, thereby altering it.

In preferred embodiments of the present invention the enzymatic RNA molecule is formed in a hammerhead motif, but the ribozyme may also be formed in the motif of a hairpin, hepatitis delta virus, group I intron or RNAse P RNA (in association with an RNA guide sequence). Examples of hammerhead motifs are described by Rossi et al., AIDS Res. Hum. Retrovir. 8:183 (1992), hairpin motifs are described by Hampel et al., Biochem. 28:4929 (1989) and Hampel et al., Nucl. Acids Res. 18:299 (1990), the hepatitis delta virus motif is exemplified in Perrotta and Been, Biochem. 31:16 (1992), an RNAseP motif is described in Guerrier-Takada et al., Cell 35:849 (1983), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target HCV RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 6 to 12, and results in base pairing to the substrate sequence immediately upstream and downstream of the N-SMase mRNA sequences which comprise the cleavage site.

In addition to the ribozymes described herein, other ribozymes specific for N-SMase mRNA may be identified. For example, to select therapeutically useful ribozymes specific for N-SMase mRNA, ribozymes are selected and expressed in whole cells. An optimized expression cassette for the ribozyme can be used where the sequence is embedded in a stable loop region which, in turn, is part of an adenoviral va RNA, so that a catalytic secondary structure can form independently from the surrounding RNA of the expressed RNA. A library of ribozymes flanked by random sequences are cloned into the loop region of the expression cassette. Ribozymes are selected from the library using the N-SMase mRNA target sequence itself. Using this strategy a ribozyme is selected for cleavage sites that are accessible within target N-SMase mRNA and that have structures that permit efficient cleavage. To confirm the effectiveness of the ribozymes in mammalian cells, cells are transfected with the ribozyme expression cassette. The resulting cleavage of N-SMase mRNA by a ribozyme produces a 5'OH group and a 2'–3' cyclic phosphate group, thereby creating an unstable molecule and decreasing the N-SMase mRNA concentration within the cell. Ribozyme producing cell lines are compared for the production of N-SMase mRNA and those ribozymes with optimal activity are selected. Ribozymes directed against different target sites in the N-SMase mRNA can be simultaneously isolated using this procedure.

The site of cleavage in a target N-SMase mRNA molecule is also dependent on the type of ribozyme, e.g., when the ribozyme is of the hammerhead type, the substrate cleavage site is immediately 3' to the sequence NUH, where N is any nucleotide, U is uridine, and H is any nucleotide except G. Different types of ribozymes can be used to achieve the specific cleavage of the targeted N-SMase mRNA molecule, e.g., different hammerhead ribozymes (at least 14 different members of this class), the larger Group I introns, RNAse P (which targets tRNA), hairpin ribozymes, hepatitis delta virus ribozyme, etc.

The term "fragment" or "derivative" when referring to an N-SMase antisense ribozyme, means RNA molecules which retain essentially the same biological function or activity as the ribozyme of SEQ ID NO:1. As used herein the term "activity", when referring to the ribozymes of the invention, refers to the ability of the ribozyme to decrease the activity of N-SMase. For example, the ribozyme fragments or derivatives of the present invention maintain at least about 50% of the activity of the ribozyme of SEQ ID NO:1, preferably at least 75%, more preferably at least about 95% of the activity of the ribozyme of SEQ ID NO:1, as determined e.g. by a standard activity gel assay such as the assay disclosed in Example 1, part 6 of U.S. Pat. No. 5,919,687, and includes measuring activity of the N-SMase peptide using [$^{14}$C]-sphingomyelin. In a preferred embodiment, the ribozymes of the invention can decrease the activity of N-SMase by at least about 2-fold, at least about 3-fold, or, most preferably, at least about 4 fold as compared to N-SMase activity in the absence of the ribozyme. In another preferred embodiment, the ribozymes of the invention can decrease the activity of N-SMase to about 2.0, 1.75, 1.5, 1.25, 1.0, 0.75, or preferably, 0.67 nmol/mg protein/hr. In another preferred embodiment, the activity of N-SMase includes the measurement of N-SMase protein or mRNA levels. Preferably, the ribozymes of the invention can decrease the expression level of N-SMase protein or mRNA by at least about 2-fold, at least about 3-fold, or, most preferably, at least about 4-fold as compared to N-SMase activity in the absence of the ribozyme.

A ribozyme fragment or derivative of the invention may be an RNA molecule in which one or more of the ribonucleotides are substituted with another ribonucleotide, including modified ribonucleotides.

The ribozyme fragments and derivatives of the invention are of a sufficient length such that they maintain ribozyme activity. Ribozyme fragments and derivatives thus preferably comprise at least 150 nucleotides, usually at least about 170 nucleotides, more usually at least about 190 amino acids, still more typically at least about 200 nucleotides, even more typically at least about 205 or 210 nucleotides. Preferred ribozyme fragments or derivatives of the invention include those that have at least about 70 percent homology (sequence identity) to the ribozyme of SEQ ID NO:1, more preferably about 80 percent or more homology to the ribozyme of SEQ ID NO:1, still more preferably about 85 to 90 percent or more homology to the ribozyme of SEQ ID NO:1.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The nucleotides at corresponding nucleotide positions are then compared. When a position in the first sequence is occupied by the nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two nucleotide sequences is determined using the GAP program in the GCG software package (available at online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (Comput. Appl. Biosci. 4:11–17 (1988)) which has been incorporated into the ALIGN program (version 2.0 or version 2.0U), using a PAM120 weight residue table, a gap length penalty of 12 and a gap penalty of 4.

N-SMase ribozymes and fragments and derivatives thereof of the invention are "isolated", meaning the ribozymes constitute at least about 70%, preferably at least about 85%, more preferably at least about 90% and still more preferably at least about 95% by weight of the total nucleic acid in a given sample. A ribozyme of the invention preferably is also at least 70% free of contaminants, more preferably at least 85% free, still more preferably at least 90% free and even more preferably at least 95% free of contaminants. The N-SMase ribozyme fragments and derivatives may be present in a free state or bound to other components.

Isolated N-SMase ribozymes and/or fragments or derivatives of the invention are preferably produced by standard recombinant methods. A wide variety of molecular and biochemical methods are available for generating and expressing the N-SMase of the present invention; see e.g. the procedures disclosed in *Molecular Cloning, A Laboratory Manual* (2nd Ed., Sambrook, Fritsch and Maniatis, Cold Spring Harbor), *Current Protocols in Molecular Biology* (Eds. Ausubel, Brent, Kingston, More, Feidman, Smith and Struhl, Greene Publ. Assoc., Wiley-Interscience, NY, N.Y. 1992) or other procedures that are otherwise known in the art. For example, N-SMase ribozymes or fragments thereof may be obtained by chemical synthesis, expression in bacteria such as E. coli and eukaryotes such as yeast, baculovirus, or mammalian cell-based expression systems, etc., depending on the size, nature and quantity of the ribozyme or fragment. The use of mammalian-based expression systems, particularly human, is particularly preferred where the ribozyme is to be used therapeutically.

Nucleic acids encoding the novel ribozymes of the present invention and fragments and derivatives thereof may be part of expression vectors and may be incorporated into recombinant cells for expression and screening, transgenic animals for functional studies (e.g. the efficacy of candidate drugs for disease associated with expression of a N-SMase), etc.

The nucleic acids of the present invention are isolated, meaning the nucleic acids comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The nucleic acids of the present invention find a wide variety of applications including: use as translatable transcripts, hybridization probes, PCR primers, therapeutic nucleic acids, etc.; use in detecting the presence of ribozyme transcripts; and use in gene therapy applications.

USES AND METHODS OF THE INVENTION

To inhibit N-SMase activity, nucleic acid encoding a ribozyme of the invention can be administered to a cell or a subject. The nucleic acids may be operably linked to gene regulatory sequences. Cells are transfected with a vector comprising a ribozyme fragment sequence with a promoter sequence oriented such that transcription of the gene yields an ribozyme transcript capable of binding to endogenous N-SMase encoding mRNA. Transcription of the antisense nucleic acid may be constitutive or inducible and the vector may provide for stable extrachromosomal maintenance or integration. Alternatively, single stranded nucleic acids may be administered to the target cell, in or temporarily isolated from a host, at a concentration that results in a substantial reduction in expression of the activity of N-SMase.

The ribozyme nucleic acids are introduced into the target cell by any method which will result in the uptake and expression of the nucleic acid by the target cells. These can include vectors, liposomes, naked DNA, adjuvant-assisted DNA, catheters, etc. Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpes virus vectors such as a herpes simplex I virus (HSV) vector [A. I. Geller et al., J. Neurochem, 64:487 (1995); F. Lim et al., in DNA Cloning: Mammalian Systems, D. Glover, Ed. (Oxford Univ. Press, Oxford England) (1995); A. I. Geller et al., Proc Natl. Acad. Sci.: U.S.A. 90 7603 (1993); A. I. Geller et al., Proc Natl. Acad. Sci USA: 87:1149 (1990)], Adenovirus Vectors [LeGal LaSalle et al., Science, 259:988 (1993); Davidson, et al., Nat. Genet., 3:219 (1993); Yang et al., J. Virol., 69: 2004 (1995)] and Adeno-associated Virus Vectors [Kaplitt, M. G., et al., Nat. Genet., 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $Ca_3(PO_4)_2$ precipitation, DEAE dextran, electroporation, protoplast fusion, lipofection, cell microinjection, and viral vectors.

The vector can be employed to target essentially any desired target cell, such as a smooth muscle or cardiovascular cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., Proc. Natl. Acad. Sci. USA, 91:2076–2080 (1994); Morrison et al., Am. J. Physiol., 266: 292–305 (1994)). Other methods that can be used include catheters, intravenous, parenteral, intraperitoneal and subcutaneous injection, and oral, topical, or other known routes of administration.

Moreover, administration of a ribozyme of the invention or fragment or derivative thereof, to mammalian cells (including human cells) can reduce or abrogate TNF-α and/or Fas-L induced cell death (apoptosis) and the invention includes therapeutic methods of treating pathologies associated with overexpression or misexpression of TNF-α, Fas-L, and/or other inflammatory cytokines. In such methods, a ribozyme of the invention can be administered to a mammal (including a human) by known procedures.

The preferred therapeutic methods of the invention (which include prophylactic treatment) in general comprise administration of a therapeutically effective amount of N-SMase ribozyme or fragment or derivative thereof, or nucleic acid encoding same, to an animal in need thereof, including a mammal, particularly a human. Such treatment will be suitably administered to subjects, particularly humans, suffering from, having, susceptible to, or at risk for atheroslcerosis. The ribozymes of the invention may also be used in the treatment of other disorders in which N-SMase may be implicated, including, but not limited to, inflammatory disorders such as arthritis, osteoarthritis and Crohn's disease, obesity, diabetes, HIV, liver disorders including cirrhosis, excessive cholesterol levels, renal failure, cholesteryl ester storage disorder, cardiac disease associated with LV dysfunction, undesired vascular restensosis, neurodegeneration, and central nervous system disorders such as depression, schizophrenia and Alzheimer's disease.

For therapeutic applications, peptides and nucleic acids of the invention may be suitably administered to a subject such as a mammal, particularly a human, alone or as part of a pharmaceutical composition, comprising the peptide or nucleic acid together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy. See, for example, *Remington's Pharmaceutical Sciences*, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics often will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. Systemic administration of a nucleic acid using lipofection, liposomes with tissue targeting (e.g. antibody) may also be employed.

It will be appreciated that actual preferred amounts of a given ribozyme of the invention used in a given therapy will vary to the particular active peptide or nucleic acid being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

This invention is further illustrated by the following examples, which should not be construed as limiting. The contents of all references, patents, and published patent applications cited throughout this application, as well as the sequence listing and the figures, are incorporated herein by reference.

EXAMPLES

In the following examples, the transfection reagents were purchased from Invitrogen (Carlsbad, Calif.), and Lipofectamine Plus was purchased from Life Science Technologies. All other chemicals were purchased from Sigma Chemical Company (St. Louis, Mo.). [$^{14}$C]sphingomyelin (specific activity 10,000, cpm/nmol) was purchased from American Radiolabeled Company (St. Louis, Mo.).

Example 1

Preparation of N-SMase Ribozyme Constructs and Transfection of MG63 Cells

The pU1/N-SMase ribozyme vector of the invention was constructed according to a modification of the methods of Montgomery, R. A., and Dietz, H. C. (1997) *Hum. Molec. Genet.* 4:519–525, the contents of which are incorporated by reference. Specifically, a U1 snRNA chimera was chosen because of its secondary characteristics, such as extended hair pin stem loops at both 5' and 3' ends. The U1 promoter is constitutively active and is highly expressed. The chimera was produced by removal of the SM protein binding sequence between the hairpin structures, with an insertion of 30 base pairs of complementary RNA interrupted at its center by a 22 base pair hammerhead ribozyme. The N-SMase cDNA sequence (U.S. Pat. No. 5,919,687; Chatterjee, S. et al. (1999) *J. Biol. Chem.* 274:37407–37412) was analyzed for sites which are easily cleaved by ribozymes, i.e., the ribonucleotide sequences GUC or GUA. An RNA folding program was used to analyze the entire structure in order to preserve the necessary stem loop structures. Two regions that were acceptable by these parameters were identified: the first in the 5-cap, prior to the ATG start site, and the second in the mid-portion of the small mRNA sequence.

The SV40 promoter, polyA, and polylinker were excised from the pZeoSV (Invitrogen) prokaryotic/eukaryotic expression vector at the BamHI sties. A U1 snRNA expression cassette was ligated into the BamHI sites of the modified pZeoSV. Unique EcoRI and SpeI restriction sites were introduced flanking the Sm protein binding site by site-directed mutagenesis. Two complementary oligonucleotides were synthesized to include the 24 highly conserved nucleotides of hammerhead ribozymes, as well as the U1 snRNA stem-loops. These oligonucleotides were annealed at 40° C. such that the remaining 5' and 3' overhangs were exactly complementary to the overhangs left by the EcoRI and SpeI digests of the vector. After ligation of the oligonucleotide duplex into the vector (now pNSMRz), the sequence of the insertion was confirmed. The corresponding sequence was analyzed using a computer program that predicts RNA secondary structure. After confirmation of the correct sequence, the circularized plasmid was linearized with ApaI and gel purified. The sequence of the ribozyme is shown in FIG. 1. A control sham-ribozyme that targeted the β-galactosidase gene, LacZ, was also used.

MG63 osteosarcoma cells that express N-SMase were grown to approximately 60% confluence and transfected with either linearized pNSMRz or an unmodified reporter gene construct (pZeoSVLacZ, Invitrogen), used as a control The transfections were performed using Lipofectamine Plus (Life Technologies) according to the manufacturer's instructions. Cells were grown in MEM media (Cellgro, Herndon, Va.) with 10% fetal calf serum and 250 μg/ml zeocin (Invitrogen). Stable incorporation of the ribozyme was selected with zeocin after 48 hours, as the U1 snRNA construct contains the zeocin-resistance gene. Individual clones were selected with cylinders, expanded to T-75 flasks and frozen in liquid nitrogen.

Cell death was evident after 48 hours. To remove dead and dying cells, cultures were rinsed daily with phosphate buffered saline (PBS) and overlaid with fresh zeocin-containing medium. After 14 days, widely spaced clonal colonies of 10–100 cells were observed and harvested using 8×8 mm cloning cylinders. After treatment with trypsin, cells were transferred to single wells of 24-well tissue culture plates and were clonally expanded Zeomycin selection (250 μg/ml). was maintained throughout all phases of experimentation. Ninety-six clones were selected for Northern analysis.

RNA was originally extracted from a single confluent (90%) T-75 flask using Trizol. Northern analysis showed very low levels of transcription in the control ribozyme-transfected cells. Next, poly-$A^+$ RNA was extracted from 3 confluent T-75 flasks, loading 3.5 μg/lane. Northern gels were standard, using 1.2% agarose, 1×MOPS, and 6.5% formaldehyde. RNA was transferred to nylon membranes with a standard wick system. The cDNA probe was derived from the cDNA construct, pHH11. An EcoR-1/SpeI fragment, containing a three hundred base pair probe was prepared. This was radiolabeled with [$^{32}$P]-dCTP and the random primer labeling system.

Figure 3:
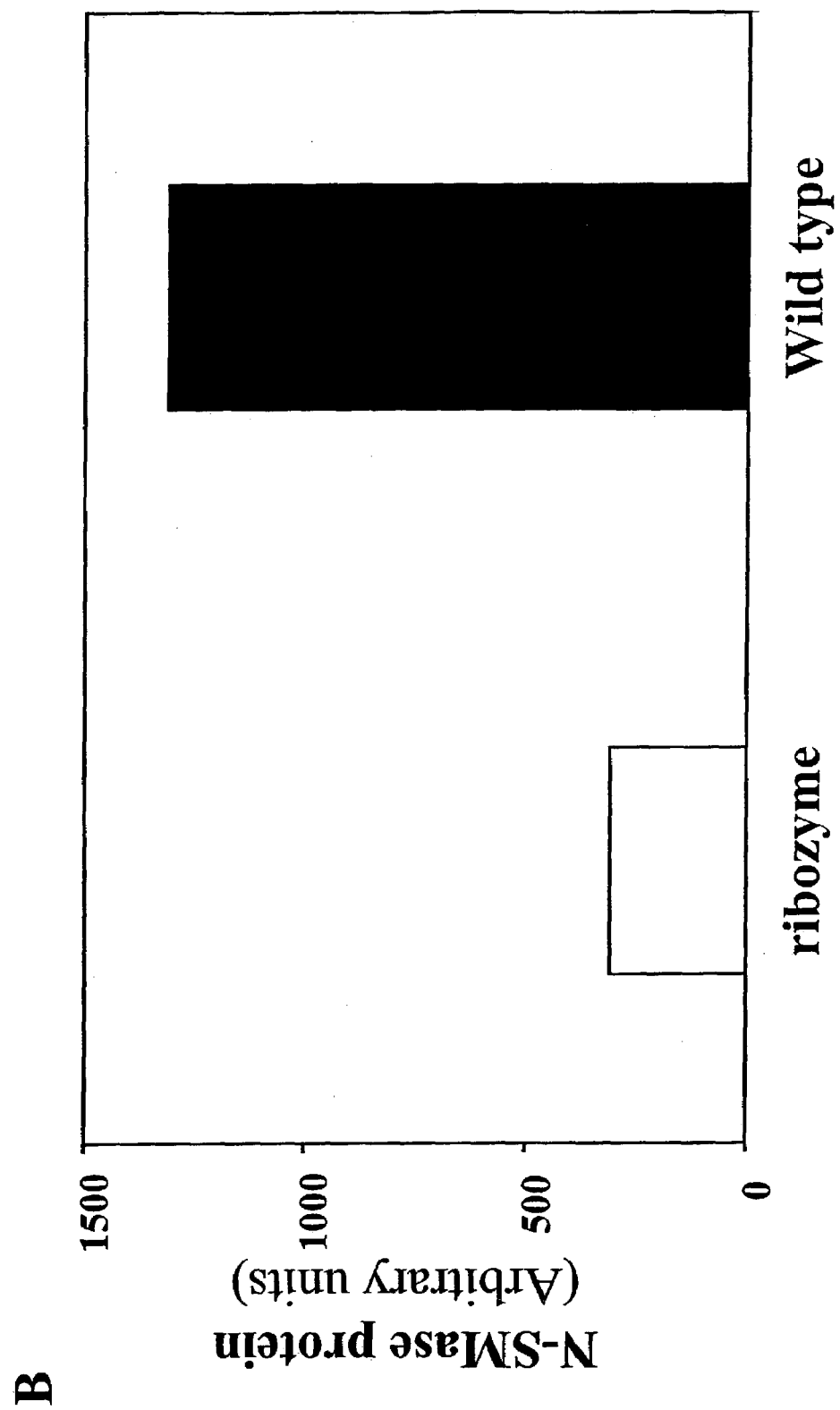
FIG. 3 depicts a western immunoblot assay and densitometric analysis of N-SMase. About 10 µg of partially purified N-SMase preparations from WT (MG-63) and mutant (CC) cells were solubilized and subjected to 7.5% polyacrylamide SDS gel electrophoresis. The proteins were then transferred to PVDF membranes and subjected to a western immunoblot assay employing an N-SMase antibody or β-actin antibody (control). The immunoreactive protein bands were then subjected to densitometric scanning.

Clone CC had no detectable N-SMase mRNA by Northern analysis, so RT-PCR was performed to quantitate the reduction. Compared to a control-transfected clone (WT), there was a 50% reduction in mRNA in clone CC (ribozyme). This was confirmed by western blot analysis of the transfected and control clones for N-SMase. Densitometric scanning of the immunoreactive bands from the western analysis is shown in FIG. 3.

Clones with reduced N-SMase mRNA were analyzed for N-SMase activity as described below. The clone with the lowest demonstrable N-SMase activity is referred to herein as the "ribozyme transfected clone".

Example 2

Immunocytotichemical Analysis of Cells

Wild-type (WT) MG-63 cells and MG-63 cells transfected with LacZ constructs (L-3) and ribozyme expression constructs for the inhibition of N-SMase expression (CC) were analyzed by immunocytochemistry. The antibodies either recognized epitopes in fibronectin (control) or N-SMase. The analysis was performed in duplicates for the MG-63 cell line and the two mutant colonies. Immunohistochemical staining for N-SMase demonstrates near absence in clone CC, compared to both untransfected (WT) and sham-transfected (LacZ) lines. No differences were observed between the lines harboring pU1/N-SMase, pZeoSVLacZ, or untransfected cells upon immunohistochemical anaylsis with a monoclonal antibody to fibronectin, suggesting that the chimeric cRNA did not globally impair pre-mRNA splicing or protein expression and metabolism.

Example 3

Activity of Acid and Neutral Sphingomyelinase in MG-63 (WT) and Mutant Cells

Confluent culture of cells were harvested, washed, and pellets lysed in buffer containing 0.1% Triton™ X-100, 25 mM Tris (pH 7.4) buffer, 5 mM EDTA, 1 mM phenylmethylsulfonylfluoride and 2 μg each of chymostatin, leupeptin, antipain, and pepstatin A. The activity levels of acid and neutral sphingomyelinase were measured in cell extracts (100 μg protein) in duplicate as described previously employing [$^{14}$C]-sphingomyelinase as the substrate.

Activities of A-SMase and N-SMase were also measured according to methods described in Chatterjee, S. and Ghosh, N. (1996) *Glycobiology* 6:303–311, incorporated herein by reference, with minor modifications. In brief, 5×10$^6$ MG63 cells were scraped from the culture plates, washed with PBS, and disrupted by repeated passage through a 25-gauge needle. Nuclei and cell debris were pelleted at 800×g for 5 min. Supernatant fluid was collected, and the protein concentration was measured using the Bio-Rad (Hercules, Calif.) protein detection kit. To measure SMase activity, 50 μg of protein was incubated for 90 min (the reaction was linear for up to 120 min) at 37° C. in buffer (200 μl final volume) containing 250 mM sodium acetate and 1 mM EDTA, pH 5.0, for A-SMase or 250 mM Tris-Cl, pH 7.4, with or without 6 mM MgCl$_2$ for N-SMase, and 0.75 μl of [methyl-$^{14}$C]sphingomyelin (SM) (0.2 mCi/ml; 56.6 mCi/mmol). Radioactive phosphocholine produced from [$^{14}$C] SM was extracted with 800 μl of chloroform-methanol (2:1, vol/vol) and 100 μl of H$_2$O. [$^{14}$C]phosphocholine in the aqueous phase was measured by scintillation counting.

A three-fold reduction in N-SMase activity was identified, with no discernable reduction in A-SMase activity, in ribozyme-transfected cells, as compared to sham-transfected and untransfected controls. The results presented below in Table I represent average value from two separate batches of cell pellets.

TABLE I

| | Sphingomyelinase Activity | |
| Cell line | Acid SMase (nmol/mg protein/hr) | Neutral SMase (nmol/mg protein/hr) |
|---|---|---|
| MG-63 (WT) | 2.7 | 2.7 |
| CC (mutant) | 2.1 | 0.67 |
| C-B (mutant) | 2.2 | 1.0 |
| L-3 (LacZ/sham) | 2.3 | 2.1 |

Example 4

N-SMase Activity in Mutant and WT Cells

Figure 2:
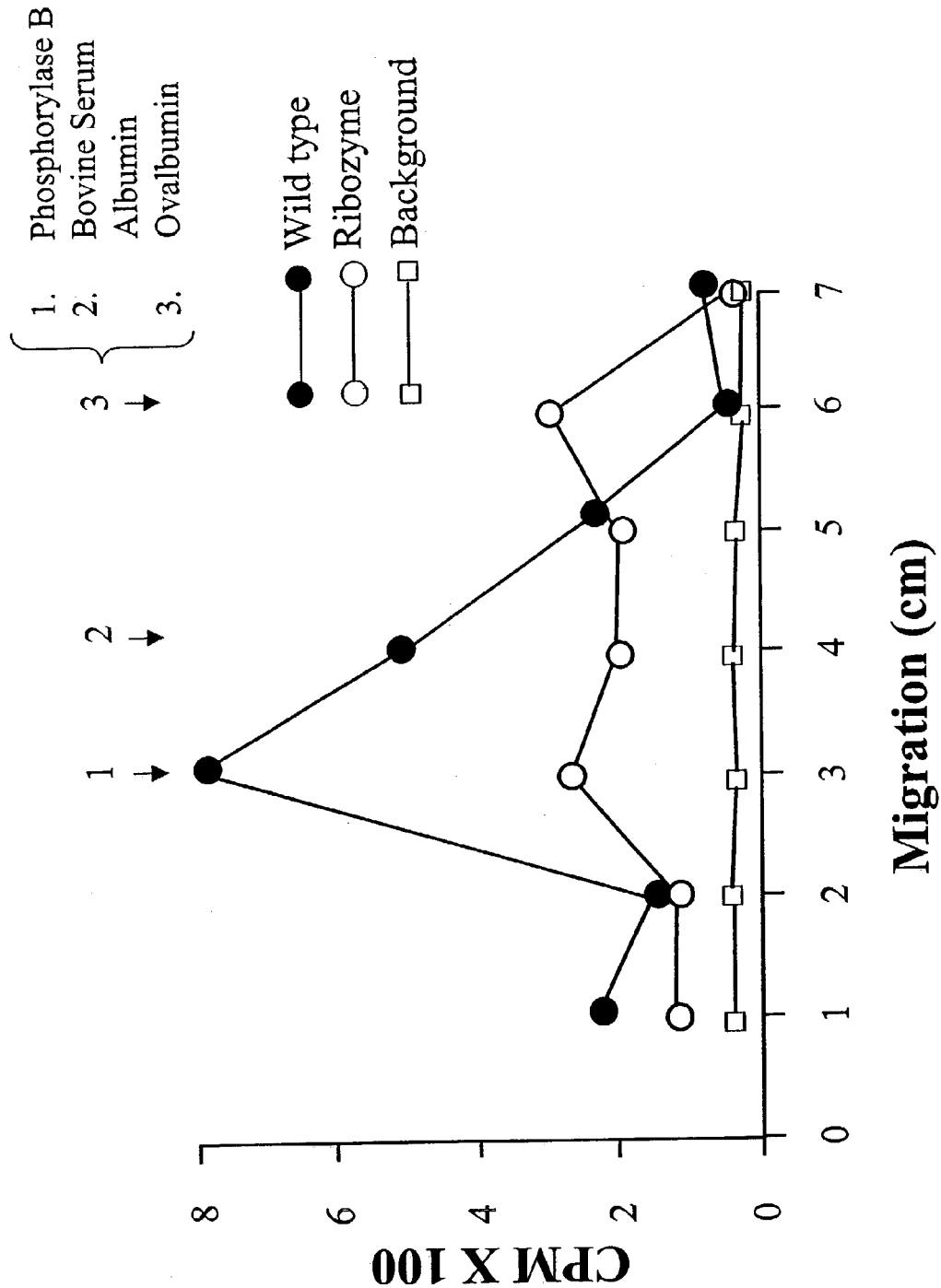
FIG. 2 depicts N-SMase activity in mutant and WT cells, as determined using gel analysis. Partially purified preparations of the MG-63 (WT) cell line and the mutant cell line CC were subjected to 7.5% polyacrylamide gel electrophoresis at 4° C. employing sodium lauryl sarcosine as the detergent. The gel was calibrated with pre-stained protein molecular weight standards (phosphorylase B, bovine serum albumin (BSA), and ovalbumin). Gel slices were excised and subjected to an N-SMase assay employing [$^{14}$C] sphingomyelinase as the substrate.

N-SMase activity in mutant and WT cells (subjected to detergent extraction as described above), was determined using gel analysis. Partially purified preparations of the MG-63 (WT) cell line and the mutant cell line CC were subjected to 7.5% polyacrylamide gel electrophoresis at 4° C. employing sodium lauryl sarcosine as the detergent. The gel was calibrated with pre-stained protein molecular weight standards (phosphorylase B, bovine serum albumin (BSA), and ovalbumin; Bio-Rad). Gel slices were excised, transferred to glass tubes, and subjected to an N-SMase assay at pH 7.4 employing [$^{14}$C]sphingomyelinase as the substrate. As shown in FIG. 2, the level of N-SMase activity in CC mutant cells is greatly reduced, as compared to control cells.

Example 5

Western Immunoblot Assay and Densitometric Analysis of N-SMase

Western immunoblot assay and densitometric analysis was used to quantify the level of N-SMase in WT and CC cells. About 10 µg of partially purified N-SMase preparations from WT (MG-63) and mutant (CC) cells were solubilized and subjected to 7.5% polyacrylamide SDS gel electrophoresis. The proteins were then transferred to PVDF membranes and subjected to a western immunoblot assay employing an N-SMase antibody. The immunoreactive protein bands were then subjected to densitometric scanning. As shown in FIG. 3, the mutant CC cells show a greatly reduced level of N-SMase.

Example 6

Effects on TNF-α and Fas Ligand Induced N-SMase Activity in WT and Mutant Cells

Figure 4A:
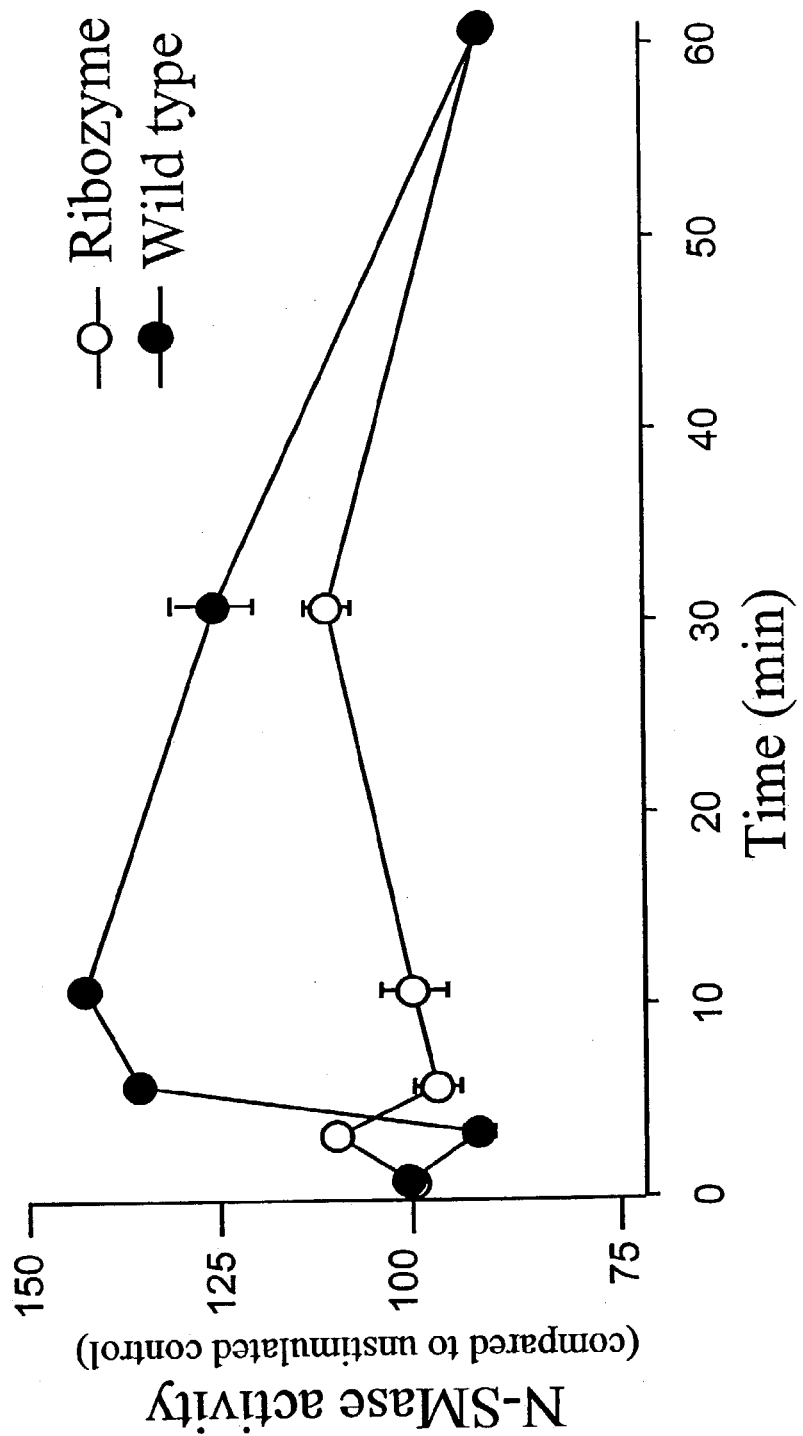
FIGS. 4A–4B depict the effects of incubation with TNF-α (FIG. 4A) and Fas ligand (FIG. 4B) over time on the activity of N-SMase in mutant and WT cells. Confluent cultures of WT (MG-63) and mutant (CC) cells were incubated with serum free medium with or without TNF-α (20 nM) or Fas ligand (1 ng/ml). At the indicated intervals, cells were harvested, centrifuged, and lysed in buffer containing 0.1% Triton™ X-100, 25 mM Tris (pH 7.4), 5 mM EDTA, 1 mM phenylmethylsulfonyl fluoride (PMSF), and 2 µg each of chymostatin, leupeptin, antipain, and pepstatin A. 100 µl of a reaction mixture containing 50 mM Tris (pH 7.4), 5 mM MgCl$_2$, 0.05% Triton™ X-100, 5 mM dithiothreitol (DTT) and 10 nmol [$^{14}$C] sphingomyelin (100,000 cpm) was added to 5–10 µl of cell lysate (100 µg protein). The basal activity of N-SMase was 2.7±0.1 nmol/mg protein/hr in MG63 cells and 0.67±0.1 nmol/mg protein/hr in CC cells. These levels were defined as 100% activity. Error bars indicate ±S.D. (N=3).
Figure 4B:
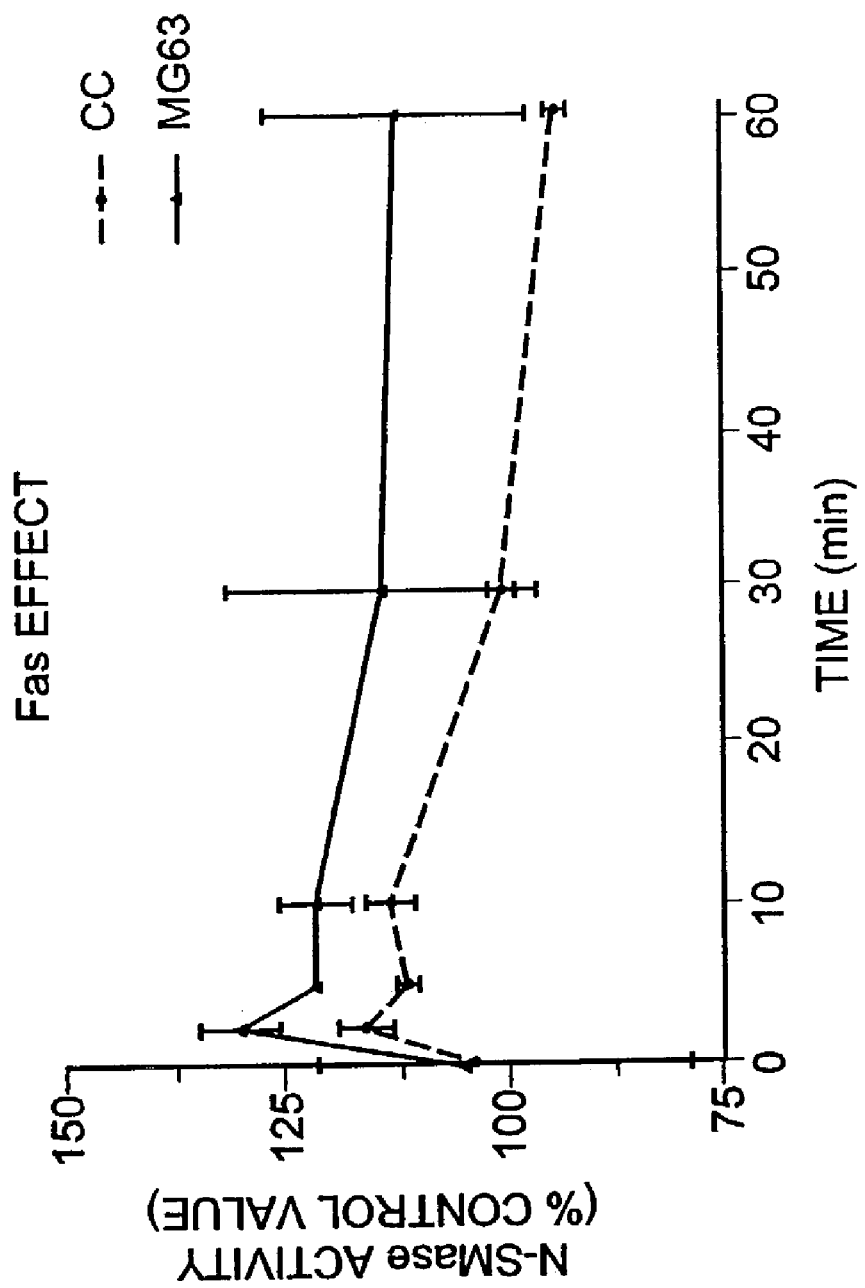

Tumor necrosis factor alpha (TNF-α) is known to induce programmed cell death through stimulation of sphingomyelinase activity and generation of ceramide. This example describes the ability of the ribozyme directed against N-SMase to inhibit this pathway. The effects of incubation with TNF-α and Fas ligand over time on the activity of N-SMase in mutant and WT cells are shown in FIGS. 4A and 4B, respectively. Confluent cultures of WT (MG-63) and mutant (CC) cells were incubated with serum free medium with or without TNF-α (20 nM) or Fas ligand (1 ng/ml), and the activity of N-SMase was determined by measuring the cleavage of [$^{14}$C]sphingomyelin. At 0, 10, 20, 30, 40, 50, and 60 minutes, cells were harvested, centrifuged, and lysed in buffer containing 0.1% Triton™ X-100, 25 mM Tris (pH 7.4), 5 mM EDTA, 1 mM phenylmethylsulfonyl fluoride (PMSF), and 2 µg each of chymostatin, leupeptin, antipain, and pepstatin A. 100 µl of a reaction mixture containing 50 mM Tris (pH 7.4), 5 mM MgCl$_2$, 0.05% Triton™ X-100, 5 mM dithiothreitol (DTT) and 10 nmol [$^{14}$C]sphingomyelin (100,000 cpm) was added to 5–10 µl of cell lysate (100 µg protein). The basal activity of N-SMase was 2.7±0.1 nmol/mg protein/hr in MG63 cells and 0.67±0.1 nmol/mg protein/hr in CC cells. These levels were defined as 100% activity. Control transfected clones reached a peak of N-SMase activity by 10 minutes after addition of TNF-α, with the activity rising to 140% of unstimulated cells. In contrast, there was no significant difference in the activity of N-SMase in ribozyme transfected cells (FIG. 4A).

Example 7

Figure 5A:
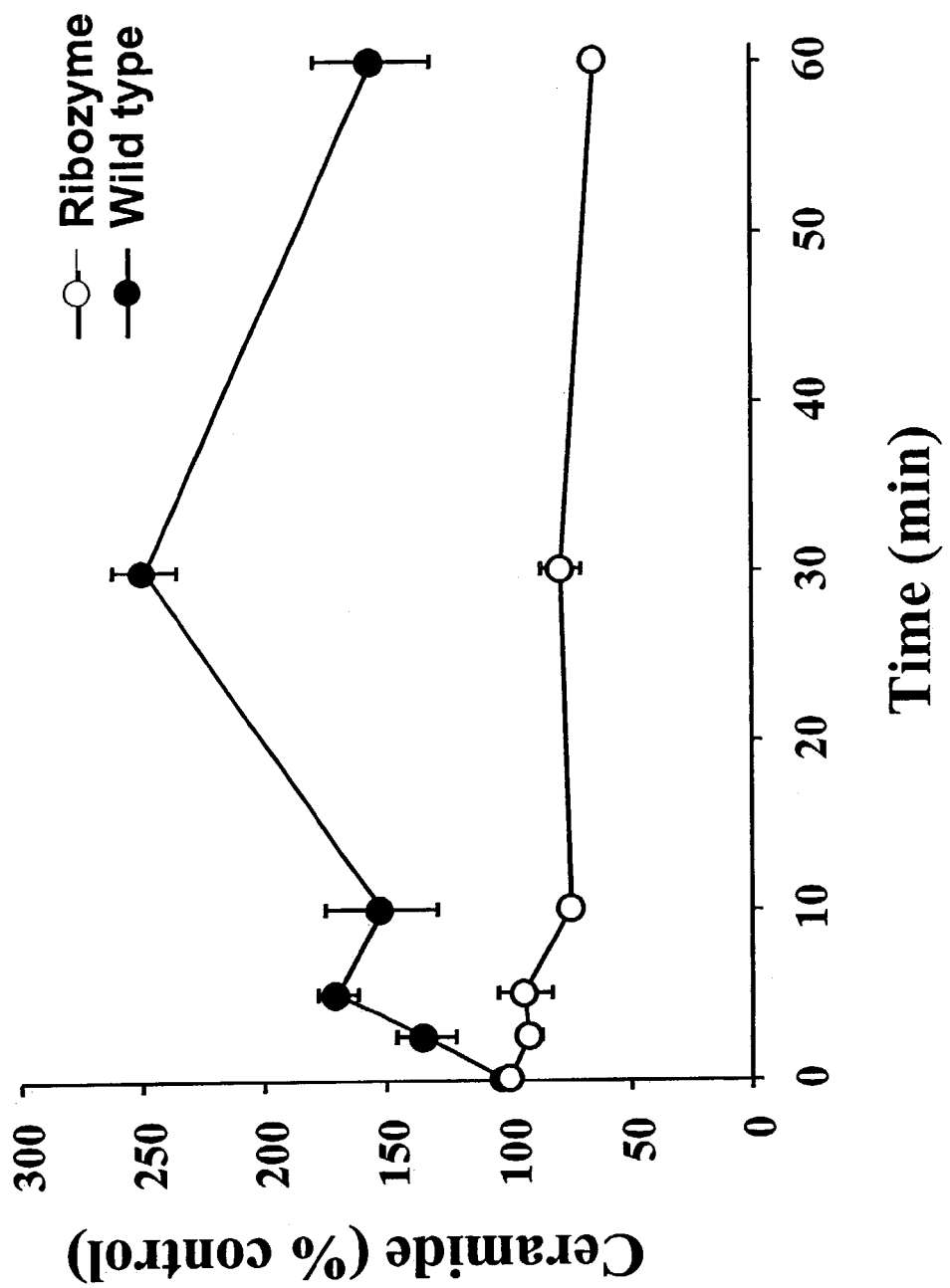
FIGS. 5A–5B depict the effects of incubation with TNF-α (FIG. 5A) and Fas ligand (FIG. 5B) over time on the level of ceramide production by N-SMase in mutant (MG-63) and WT (CC) cells. Cells (1×10$^3$) were seeded in 96-well sterile plastic trays. Upon confluence, the culture medium was replaced with serum-free minimum essential medium, plus TNF-α (20 ng/ml) or Fas-L (1 ng/ml). After incubation for 24 hours at 37° C., the cells were harvested and ceramide levels were determined using the modified diacylglycerol kinase assay. The basal level of ceramide production was 2.63 pmole/mg protein in MG-63 cells and 4.59 pmole/mg protein in CC. The results represent ±S.D. of three experiments.
Figure 5B:
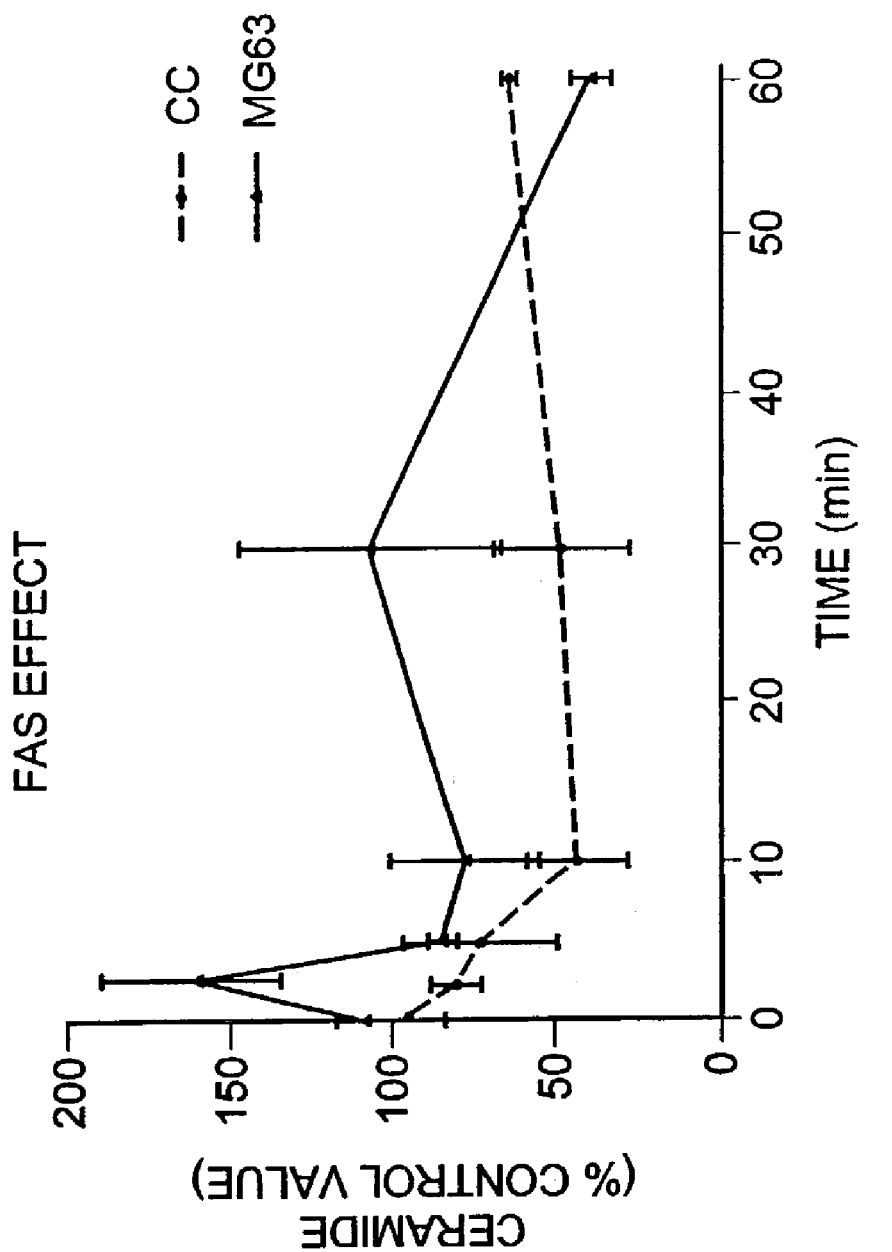

Effects on TNF-α and Fas Ligand Induced Ceramide Production by N-SMase in WT and Mutant Cells This example describes the effects of incubation with TNF-α (FIG. 5A) and Fas ligand (FIG. 5B) over time on the level of ceramide production by N-SMase in mutant (MG-63) and WT (CC) cells. Cells (1×10$^3$) were seeded in 96-well sterile plastic trays. Upon confluence, the culture medium was replaced with serum-free minimum essential medium, plus TNF-α (20 ng/ml) or Fas-L (1 ng/ml). After incubation for 24 hours at 37° C., the cells were harvested and ceramide levels were determined using the modified diacylglycerol kinase assay. The basal level of ceramide production was 2.63 pmole/mg protein in MG-63 cells and 4.59 pmole/mg protein in CC. Production of ceramide in response to TNF-α stimulation was severely reduced in the ribozyme transfected cells, as compared to sham transfected cells (FIG. 5A).

Example 8

Effects of TNF-α, C$_2$-Ceramide, and Fas-L on Apoptosis

Several different assessments of apoptosis were performed, and all showed marked resistance to apoptosis in cells with ribozyme-induced deficiency of N-SMase. CC cells showed a decrease in the level of apoptotic cells induced after treatment with TNF-α, C$_2$-Ceramide, or Fas-L, as compared to WT and LacZ. As shown in FIG. 6, apoptosis was inhibited in the mutant cells, as compared to WT. TUNEL staining demonstrated that both untransfected and sham-transfected cells have normal amounts of apoptosis in response to TNF-α, FasL, and C$_2$-ceramide.

However, cells deficient in N-SMase had marked hyporesponsiveness to TNF-α and FasL, though an appropriate response to C$_2$-ceramide. WT (MG-63), LacZ (L-3) and mutant (CC) cells were grown on glass cover slips and incubated for 24 hr with TNF-α (20 ng/ml), cell-permeable ceramide (C$_2$-ceramide) (10 ng/ml) or Fas-L (1 ng/ml). Cells were fixed and stained with DAPI stain and photographed (50×). Apoptotic cells were counted using a hemocytometer and compared to total cell counts per field. Basal levels of apoptosis were 3% untransfected, 3% control transfection, and 2.8% ribozyme transfection.

Quantitation of DAPI staining after treatment with TNF-α (20 ng/ml for 24 hours) showed that control-transfected cells have 490% DAPI staining compared to untransfected cells with or without TNF-α treatment (FIG. 6). Consistent with the hypothesis that an impaired response to TNF-α is due to decreased production of ceramide in the setting of diminished N-SMase, treatment with $C_2$-ceramide resulted in a greater than two-fold increase in apoptosis in N-SMase deficient cells (FIG. 6).

Figure 9:
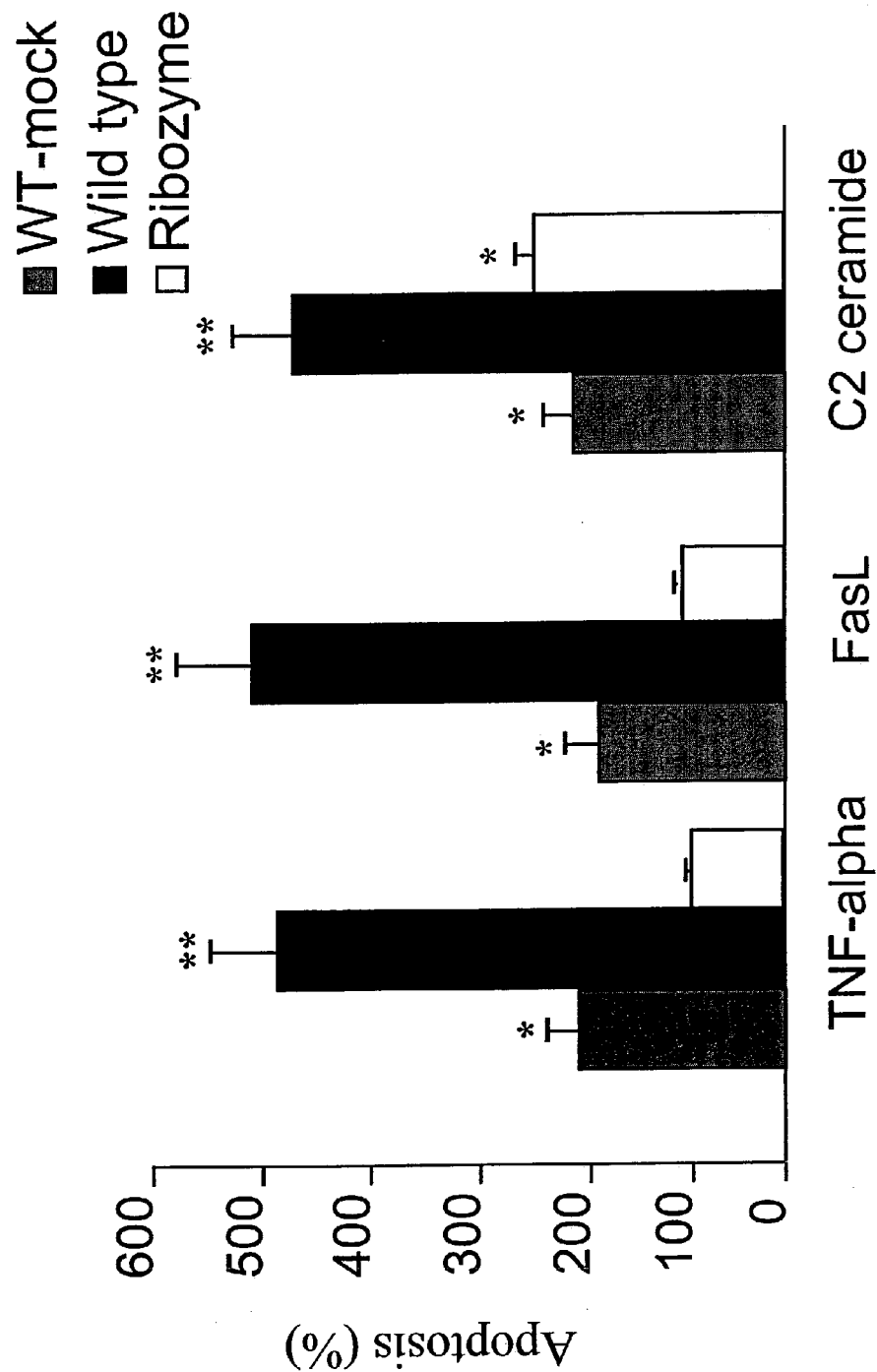
FIG. 9 depicts the effects of TNF-α and Fas-L on caspase-3 in wild type and ribozyme transfected cells. Cells were incubated for 24 hr at 37° C. with serum free minimum essential medium and various concentrations of TNF-α or Fas-L, and then processed as described in the Examples. The results represent mean ±S.D. of three experiments.
Figure 10:
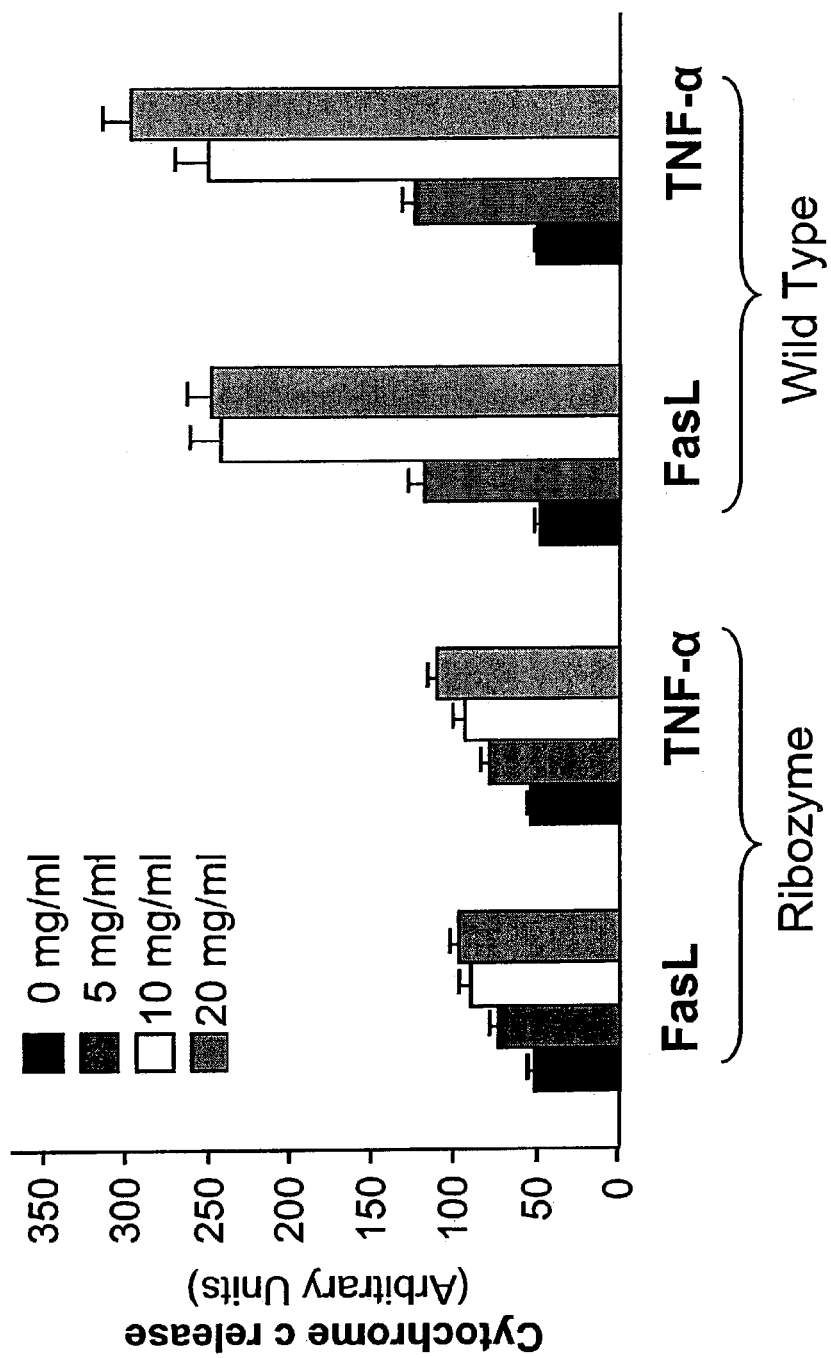
FIG. 10 depicts the effects of TNF-α and Fas-L on cytochrome c release in wild type and ribozyme transfected cells. Cells were incubated for 24 hr at 37° C. with serum free minimum essential medium and various concentrations of TNF-α or Fas-L, and then processed as described in the Examples. The results represent mean ±S.D. of three experiments.

In order to determine a dose-response relationship between the concentration of TNF-α or FasL and apoptosis, western analysis was used to quantitate release of both caspase-3 (FIG. 9) and cytochrome-C (FIG. 10).

Immunoblots for the measurement of cytochrome-C and caspase-3 were carried out after incubation of cells with TNF-α (10 ng/ml) or FasL (1 ng/ml) for 48 hours. Cells were extracted with a buffer (20 mM Hepes pH 7.5, 10 mM KCl, 1.5 mM $MgCl_2$, 5 mM EDTA, 5 mM DTT, 2 mM phenylmethylsulfonylfluoride, 1% NonidetP40, 0.5% sodium deoxycholate, 0.1% SDS, 2 µg/ml leupeptin, 2 µg/ml aprotinin, 0.5 µg/ml benzamindine, and 250 mM sucrose) on ice for 30 minutes. After centrifugation for 10 minutes at 10,000×g, the supernatant was used for western analysis with an antibody for cytochrome-C (Pharmingen, San Diego, Calif.). For assessment of caspase-3, samples were similarly processed in addition to passage through a 21-g needle prior to centrifugation. The western analysis was performed with a rabbit polyclonal IgG antibody to caspase-3 (Santa Cruz, Calif.) raises against an epitope corresponding to amino acids 1–277, representing the full-length precursor form of CPP-32 (caspase-3). For both caspase-3 and cytochrome-C, bands were quantified with densitometric analysis.

There was a linear dose-response relationship for both TNF-α and FasL in control (sham-transfected) cells, as compared to marked blunting of the response in N-SMase-deficient cells. Additional assays to confirm the reduction in apoptotic response to FasL and TNF-α included measures of caspase-3 release and cytochrome-C release.

Figure 8:
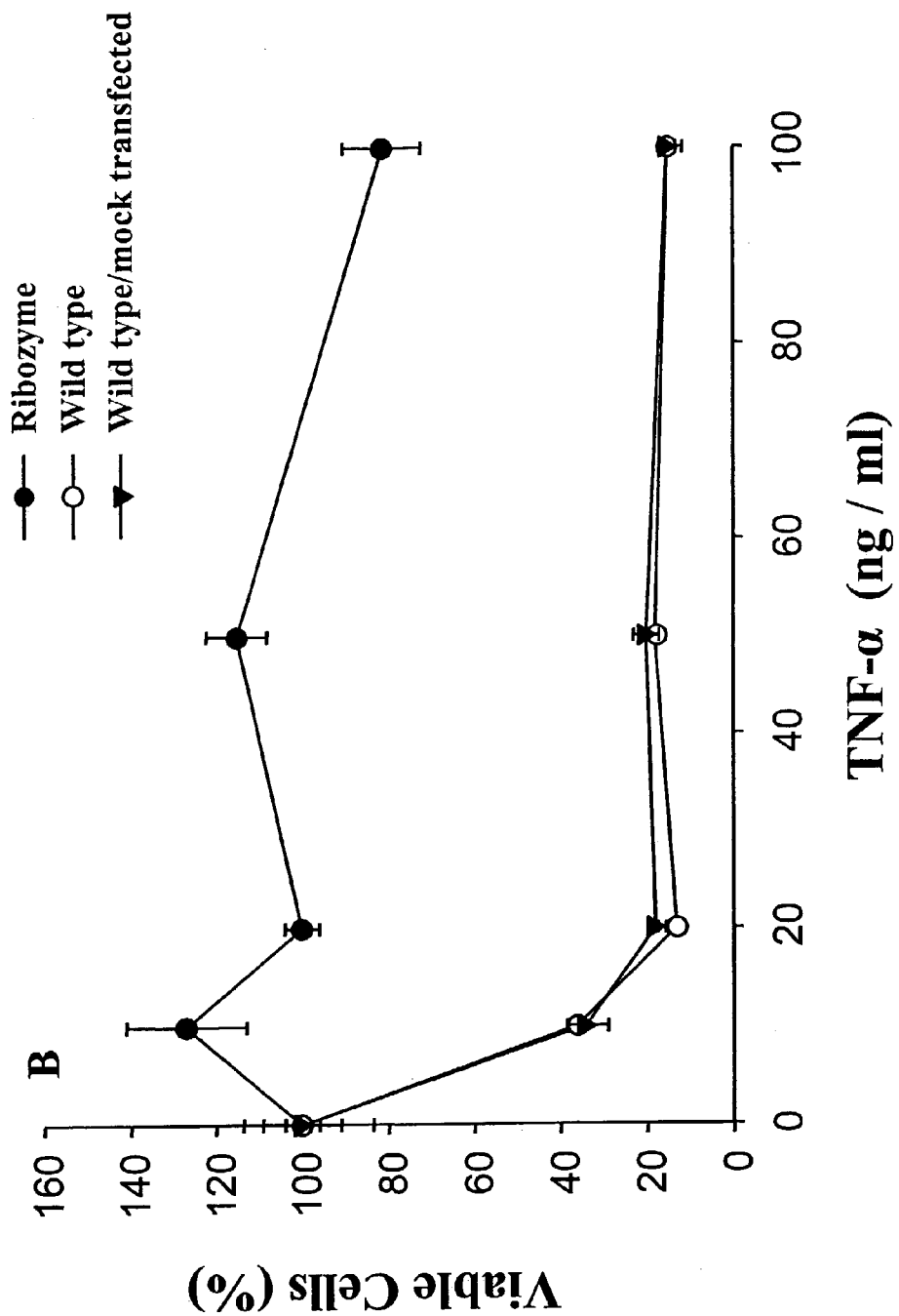
FIG. 8 depicts the effect of TNF-α on viability of wild type, ribozyme transfected and wild type/mock transfected cells. Cells (×10$^3$) were seeded in 96 well sterile plastic trays. Upon confluence medium was replaced with serum free minimum essential medium and TNF-α (20 ng/ml). After incubation for 24 h at 37° C., viability of cells were determined by Trypan blue staining. The results represent ±S.D. of three experiments.
Figure 9:
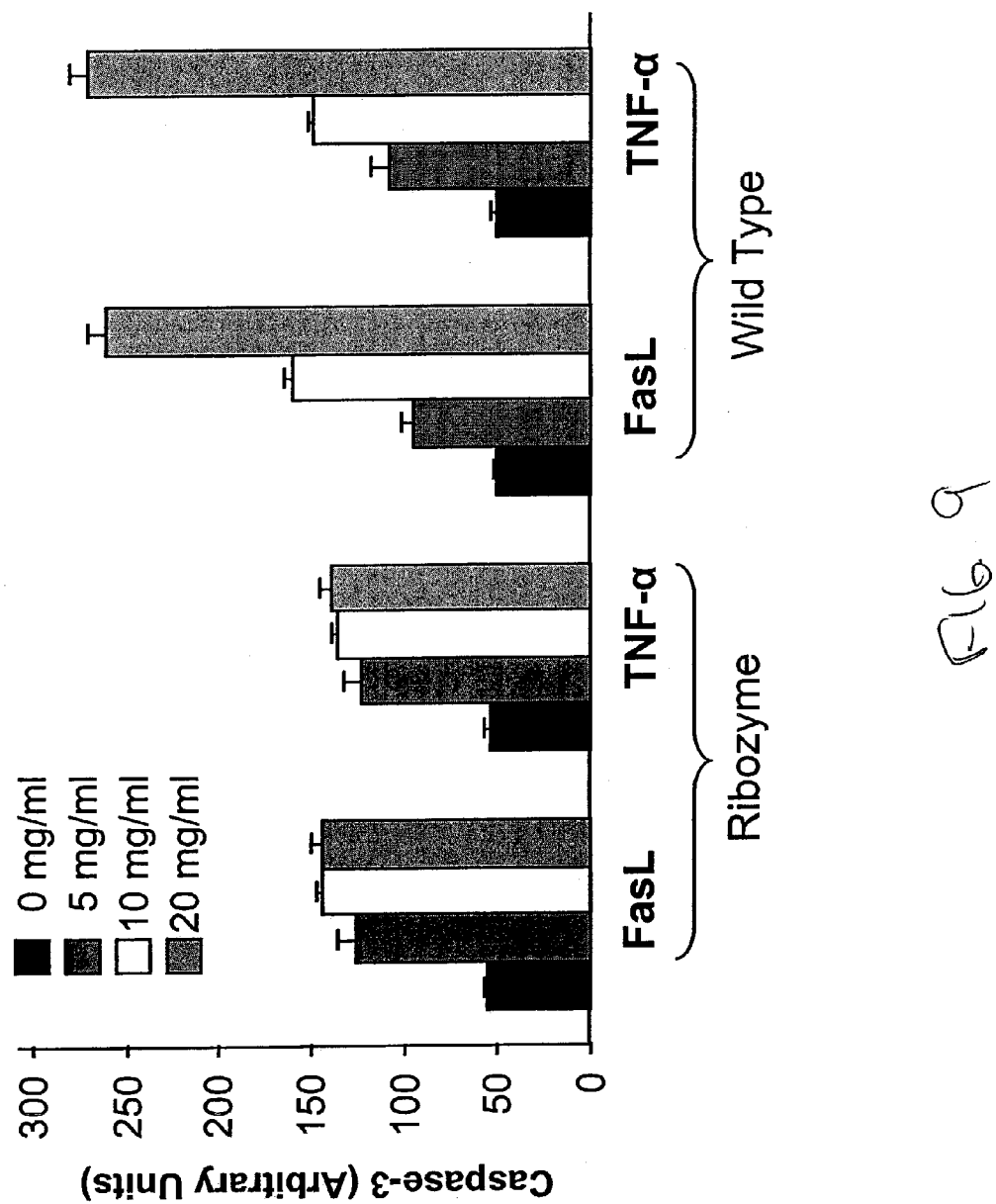

The population of viable cells was determined using trypan blue staining. Cells ($10^4$) were seeded in 96 well plates. Twenty-four hours later, the media was replaced with serum-free MEM, and TNF-α in various concentrations was added. After incubation for 24 hours at 37° C., the cells were trypsinized, and viable cells were counted after staining with trypan blue. Values were compared to the original cell count ($10^4$) and expressed as a percentage. As shown in FIG. 8, there was no significant decline in viable ribozyme transfected cells over a wide range of TNF-α concentrations, as compared to control cells, which showed a prompt decline in the population of viable cells.

Figure 7A:
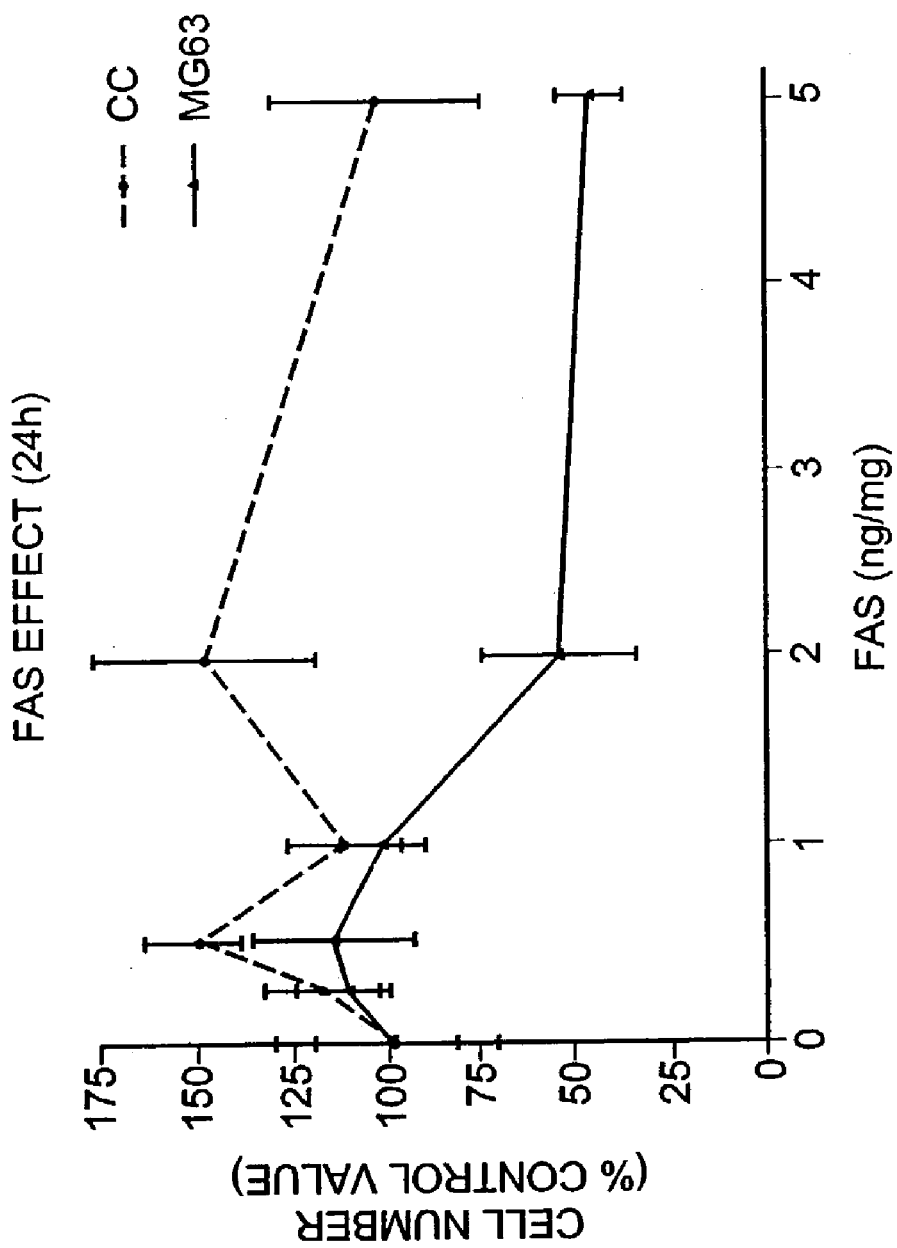
FIGS. 7A–7B depict the effects of TNF-α and Fas-L on the incorporation of [$^3$H] thymidine in WT (MG-63) and mutant (CC) cells. The cells (1×10$^3$) were seeded in 96-well sterile plastic trays. Upon confluence, the culture medium was replaced with serum-free minimum essential medium, plus TNF-α (20 ng/ml) or Fas-L (1 ng/ml). After incubation for 24 hours at 37° C., [$^3$H]-thymidine (5 mCi/ml) was added to each well. Incubation was continued for 2 hours, after which the incorporation of [$^3$H] thymidine in the cells was measured. The results represent ±S.D. of two experiments analyzed in groups of 6 wells per treatment.
Figure 7B:
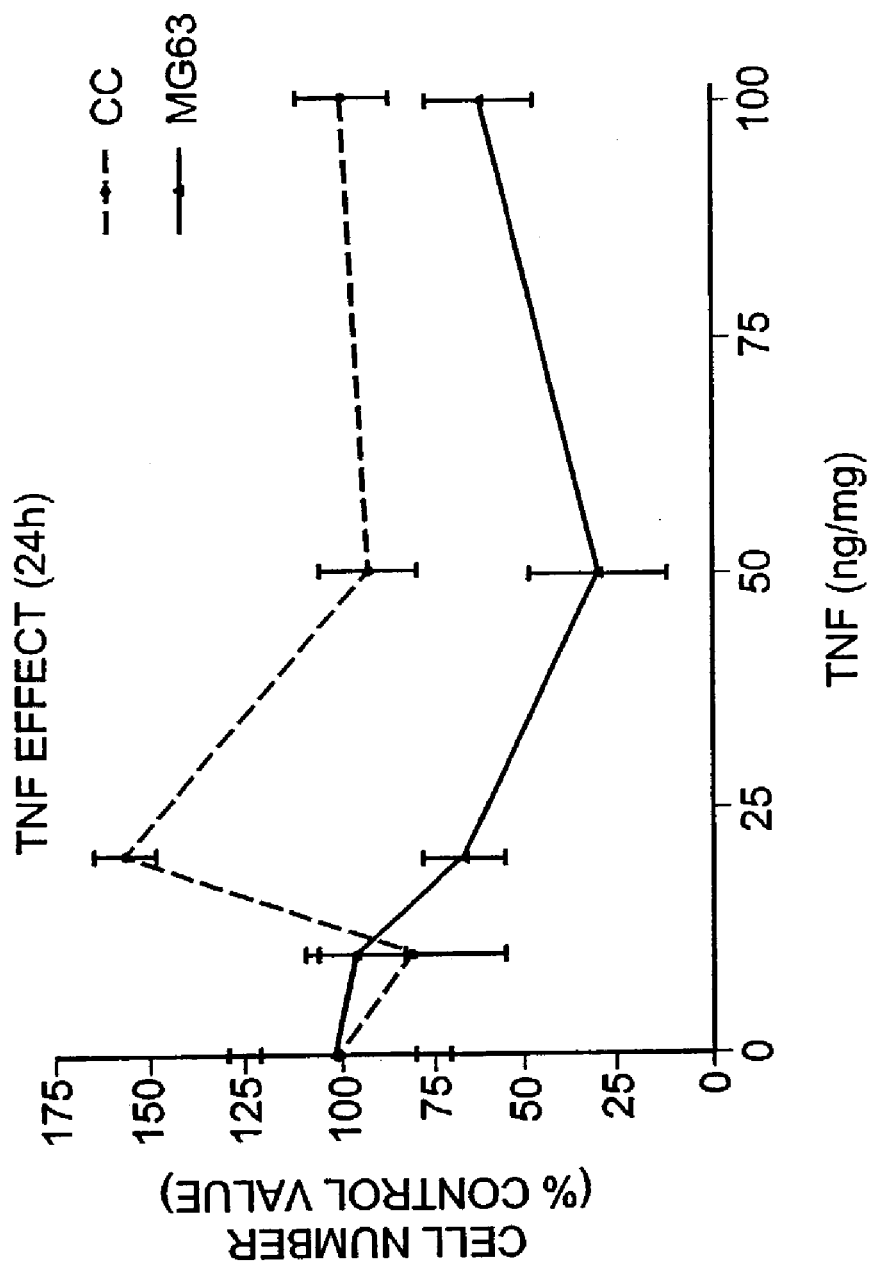

Quantitative analysis was also done by measuring [$^3$H] thymidine incorporation by proliferating cells. Cells ($1 \times 10^3$) were seeded in 96-well sterile plastic trays. Upon confluence, the culture medium was replaced with serum-free minimum essential medium, plus TNF-α (20 ng/ml) or Fas-L (1 ng/ml). After incubation for 24 hours at 37° C., [$^3$H]-thymidine (5 mCi/ml) was added to each well. Incubation was continued for 2 hours, after which the incorporation of [$^3$H] thymidine in the cells was measured. As shown in FIG. 7, proliferation of WT cells is greatly reduced as compared to WT cells.

Example 9

Quantification of Ceramide Concentration

Confluent cultures of cells were treated with TNF-α (20 ng/ml) for 24 hours and harvested, and the ceramide concentrations were determined by the modified diacylglycerol kinase assay (Signorelli, P. and Hannun, Y. A. (2002) *Methods Enzymol.* 345:275–294, incorporated herein by reference. Values shown represent percentages compared to basal levels, ±SD of three experiments. Basal levels were: 2.63 pmol/mg protein for control cells, and 4.59 pmol/mg protein for ribozyme-transfected cells.

The data presented herein demonstrate that an antisense ribozyme that specifically targets N-SMase mRNA can dramatically decrease the amount of N-SMase present in cultured cells (MG63), both by antibody staining and enzyme activity. Antibody staining for fibronectin demonstrates that the cellular membrane is intact, helping to confirm the specificity of targeting. Using several methods of detecting apoptosis in these cells, the apoptotic response to an inflammatory cytokine (TNF-α) and FasL were shown to be dramatically blunted in response to this ribozyme. Finally, the administration of cell-permeable ceramide was shown to be able to bypass the effects of this ribozyme by inducing apoptosis, confirming that the downstream effectors of this pathway are intact.

Apoptosis represents a major regulatory mechanism in the growth, development and differentiation of various organs. Morphologically, apoptosis involves loss of cell volume, plasma membrane blebbing, chromatin condensation followed by packaging of the cellular contents into membrane enclosed vesicles called "apoptotic bodies" that are taken up rapidly by neighboring cells (White, E. (1996) *Genes Develop.* 10: 1–15). Apoptosis occurs when an internally encoded suicide program is activated as a result of extrinsic/intrinsic signals (White, E. (1996) *Genes Dev.* 10: 1–15; Williams, G. T. and Smith, C. A. (1993) *Cell* 74: 777–779; Vaux, D. L. and Strasser, A. (1996) *Proc. Natl. Acad. Sci. USA* 93: 2239–2244; White, E. (1996) *Genes Develop.* 10: 1–15). Environmental factors that induce apoptosis include stress, UV light and radiation (Devary, Y. et al. (1992) *Cell* 1081–1091). Several intrinsic factors that can induce apoptosis prematurely in tissues include the various cytokines such as TNF-α, interleukin-1, and Fas/Apo-I may be relevant in auto-immune disease and neoplasms (Fisher, D. E. (1994) *Cell* 78: 539–542; Thompson, C. (1995) *Science* 267: 1456–1462). In atherosclerosis, apoptosis is often associated with the less predominant plaque, which is prone to disruption, erosion, thrombosis and restenotic lesions (Isner, J. M. et al. (1995) *Circulation* 91:2703–2711; Hegyi, L. et al. (1996) *J. Pathol.* 180: 423–429; Kockx, M. M. et al. (1996) *Atherosclerosis* 120: 115–124; Geng, Y.-J., and Libby, P. (1995) *Am. J. Pathol.* 147: 251–266; Han, D. K. M. et al. (1995) *Am. J. Pathol.* 147: 267–277; Bennet, M. R. et al. (1994) *Circ. Res.* 74: 525–536). In a study of brain graft atherosclerosis, a consistent association was found between foam cell accumulation and A-SMC death in the fibrous cap (Kockx, M. M. et al. (1996) *Circulation* 94: 1255–1262) and in cerebral atherosclerosis (Imai, H., and Thomas, W. A. (1968) *Exp. Mol. Pathol.* 8: 330–357).

The cytoplasmic domain of two cell surface receptors, Fas/apo-1 (CD95) and TNF-α-R1 that share considerable homology has been termed the "death domain". These two proteins contain cysteine-rich repeats that are also found in the nerve growth factor family of proteins including TNF-α-R2, CD26, CD30, CD40, Ox-4 and H-I BB. The ligands for Fas and TNF-α-RI are FasL and TNF-α, respectively (Vaux, D. L. (1997) *Cell* 90: 389–390). TRAIL is an orphan member of the TNF-α family and can induce apoptosis in certain target cells (White, E. (1996) *Genes Dev.* 10: 1–15).

The data presented herein demonstrate that the use of an antisense ribozyme construct specifically decreased the basal mRNA level and N-SMase activity in MG63 cells. For example, when the ribozyme-transfected cells were compared with those untransfected cells, our findings suggest that the N-SMase ribozyme did not compromise the integrity of the cell membrane, based on a normal pattern of fibronectin staining. Further, when compared to the lacZ-transfected control cells acid sphingomyelinase (A-SMase) activity was unchanged in N-SMase ribozyme transfected.

Cellular pathways known to be involved in apoptosis are as follows. Several intrinsic/extrinsic apoptotic stimuli contribute to the oligerimazation of the receptor; the adapter protein such as FADD/MORT-I (see above) directly bind to the death domain; which in turn recruits caspase-8 (FLICE/MACH) (Los, M. et al. (1995) Nature 375: 81–83). The conversion of effective caspases from the dormant pro-enzyme forms to active hetero dimer occurs. Such enzymes in turn, secrete a set of effective polypeptides (caspases) for example, cpp32 or caspase-3, which eventually leads to the hydrolysis of cytosolic and nuclear substrates contributing to apoptosis. Apoptosis is under the control of the bcl-2 family of dimerizing proteins. Bcl-2 inhibits apoptosis by preventing lipid oxidation (Hockenberry, D. M. et al. (1993) Cell 75: 241–251; Jacobson, M. D. and Raff, M. C. (1995) Nature 374: 814–816; Harada, K. et al. (1997) FEBS Lett. 411: 63–66; Korsmeyer, S. J. et al. (1995) Biochem. Biophys. Acta. 1271: 63–66; Yang, J. et al. (1997) Science 275: 1129–1132) and blocks the release of cytochrome-C from mitochondria (Sata, M. and Walsh, K. (1998) J. Clin. Invest. 9: 1682–1689). This suggests that bcl-2 functions downstream of an oxidative stimulus. TNF-α/Fas induced apoptosis may recruit FADD/FLICE as well as ceramide or its higher homolog such as GD3 and nitric oxide (NO) (Singh, I. et al. (1998) J. Biol. Chem. 273:20354–20362; Pahan, K. et al. (1998) J. Biol. Chem. 273: 2591–3000; DeMarva, R. et al. (1997) Science 277: 1652–1661). Alternatively, ceramide can directly activate caspase-3 and induce apoptosis (Mizushima, N. et al. (1996) FEBS Lett. 395: 267–271; Smyth, M. J. et al. (1996) Biochem. J. 316: 25–28; Leppanen, P. et al. (1998) Atherosclerosis 136: 147–152).

The studies presented herein have employed a variety of assays to establish that N-SMase contributes directly to apoptosis. In particular, recent studies implicate mitochondrial involvement as an integral aspect of apoptosis (Hannun , 2002. FASEB J.). Accordingly, assays to measure the release of cytochrome C, caspase activation as well as DNA fragmentation as criteria for apoptosis were used. Two diverse agonist of apoptosis i.e. TNF-α and fas/Apo-I-CD95 that have been widely used to investigate their biological activity in normal and mutant cells were employed in the experiments presented herein.

Both agonists failed to induce the activation of N-SMase activity, ceramide production and the signaling cascade above to induce apoptosis. The choice of these two apoptosis agonists was not only predicated because of their wide use, but also because TNF-α, TNF-α mRNA and fas Apo-I/CD95 is present in human atherosclerotic plaques and experimental models of atherosclerosis. In addition, the levels of both of these apoptotic agonists are elevated in inflammation (Libby, P. et al. (2002) Circulation 105: 1135–1143).

At least two distinct transmembrane signaling systems have been characterized that mediate the action of intrinsic factors such as TNF-α on apoptosis. The first one is a sphingomyelin pathway that involves the agonist/dependent hydrolysis of sphingomyelin via N-SMase as well as A-SMase to ceramide. Ceramide in turn, serves as a "second messenger" that activates caspase-3 and induces apoptosis (Pena, L. A. et al. (1997) Biochem. Pharm. 53: 615–621; Liu, B. et al. (1997) Cell and Develop. Biol. 8:311–322). The second one is the "death domain" adapter protein system, which specifically mediates the apoptosis of cytokine receptors such as TNF-α and Fas/apo-1/CD95 (White, E. (1996) Genes Dev. 10: 1–15; Williams, G. T. and Smith, C. A. (1993) Cell 74: 777–779; Vaux, D. L. and Strasser, A. (1996) Proc. Natl. Acad. Sci. USA 93: 2239–2244; White, E. (1996) Genes Dev. 10: 1–15; Devary, Y. et al. (1992) Cell 1081–1091). Human and murine acid sphingomyelinase (pH optima 4.5–5.0) have been cloned and determined to be the products of a conserved gene (Schuchman, E. H. (1999) Chem. Phys. Lipids 102: 179–188). A-SMase activity has been localized within the lysosomes, endosomes and more recently in caveolae of IL-I treated cells (Levade, T. et al. (1986) J. Clin. Chem. Clin. Biochem. 24: 205–220). Since A-SMase knockout mice retain N-SMase activity, it suggests that the neutral form of sphingomyelinase(s) are products of distinct gene(s). A $Mg^{2+}$-dependent N-SMase cDNA has been recently cloned (Tomiuk, S. et al. (1998) Proc. Natl. Acad. Sci. USA 95: 3638–3643). However, transfection of this cDNA in human embryonic kidney cells did not alter the intracellular levels of ceramide and did not stimulate TNF-α apoptosis significantly.

In contrast, the molecular cloning of a novel human kidney N-SMase that has no homology to the other neutral sphingomyelinase reported earlier has been reported (Tomiuk, S. et al. (1998) Proc. Natl. Acad. Sci. USA 95: 3638–3643). Overexpression of this cDNA in Cos-7 cells and human A-SMC increased the activity of N-SMase on the order of 5–10-fold. This was accompanied by marked apoptosis compared to cells transfected with mock cDNA. Collectively, these data provide convincing evidence that N-SMase plays an important role in TNF-α induced apoptosis. Since T-lymphocytes from patients with A-SMase deficiency (Niemann Pick disease) were insensitive to apoptosis (Santana, P. et al. (1996) Cell 86: 189–199) indicate that the A-SMase can also contribute to increased ceramide levels required for apoptosis (Pena, L. A. et al. (1997) Biochem. Pharm. 53: 615–621).

Additional studies, however, have revealed that FasL induced apoptosis in these cells can occur independent of ceramide generation (Watts, J. D. et al. (1997) Proc. Natl. Acad. Sci. USA 94: 7292–7296) and the absence of a functional A-SMase (Boesen-de Cock, J. G. R. et al. (1998) J. Biol. Chem. 273: 7560–7565). Since in our study the activity of A-SMase was unchanged in the N-SMase deficient cells yet the cells were resistant to TNF-α and fas Apo-I-CD95 induced apoptosis provides direct evidence that N-SMase is a bona fide, independent mediator of agonist induced apoptosis.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A nucleic acid molecule which is capable of cleaving an mRNA encoding N-SMase wherein the sequence of the nucleic acid molecule is at least about 95 percent identical to SEQ ID NO: 1.

2. The nucleic acid molecule of claim 1, wherein the sequence is set forth as SEQ ID NO:1.

3. A recombinant vector comprising the nucleic acid molecule of claim 1 or 2.

4. An isolated host cell comprising the vector of claim 3.

5. A nucleic acid molecule comprising the nucleotide sequence of SEQ ID NO:1, or complement thereof.

6. A recombinant vector comprising the nucleic acid molecule of claim 5.

7. An isolated host cell comprising the vector of claim 6.

* * * * *